US008202995B2

(12) United States Patent
Fan et al.

(10) Patent No.: US 8,202,995 B2
(45) Date of Patent: Jun. 19, 2012

(54) PHARMACEUTICALLY ACCEPTABLE SALTS OF APORPHINE DERIVATIVES AND CARBOXYL GROUP-CONTAINING AGENTS AND METHODS FOR PREPARING THE SAME

(75) Inventors: Chin-Tsai Fan, Sinying (TW); Cheng-Shun Lai, Sinying (TW); Mei-Jung Lin, Sinying (TW)

(73) Assignee: Standard Chem. & Pharm. Co., Ltd., Sinying (TW)

( * ) Notice: Subject to any disclaimer, the term of this patent is extended or adjusted under 35 U.S.C. 154(b) by 420 days.

(21) Appl. No.: 12/457,713

(22) Filed: Jun. 19, 2009

(65) Prior Publication Data

US 2009/0318488 A1 Dec. 24, 2009

Related U.S. Application Data

(60) Provisional application No. 61/074,246, filed on Jun. 20, 2008.

(51) Int. Cl.
*C07D 221/18* (2006.01)
*C07D 221/02* (2006.01)
(52) U.S. Cl. ............................................ 546/75; 546/61
(58) Field of Classification Search .................. 546/75, 546/61
See application file for complete search history.

(56) References Cited

U.S. PATENT DOCUMENTS 7,057,044 B2   6/2006 Su et al.
7,294,715 B2 * 11/2007 Su et al. ........................... 546/41
2003/0124503 A1   7/2003 Olivencia-Yurvati et al.

OTHER PUBLICATIONS

Orito K. et al.: Aryl radical cyclizations of 1-(2'-bromobezyl)isoquinolines with AIBN-Bu3SnH: Formation of aporphines and indoloisoquinolines. Organic Letters, vol. 2, pp. 307-310, 2000.*
Chen, Jiawei et al., Role of Oxidative Stress in Coronary Heart Disease, Indian Heart J., 2004, p. 163-173, 56.
Alexander, R. Wayne, Hypertension and the Pathogenesis of Atherosclerosis, Theodore Cooper Memorial Lecture, 1995, p. 155-161, 25, American Heart Association, Inc., United States.
Berliner, Judith A. et al., The Role of Oxidized Lipoproteins in Atherogenesis, Free Radical Biology & Medicine, 1996, p. 707-727, vol. 20, No. 5, Elsevier Science Inc., United States.
Heinecke, Jay W., Oxidants and Antioxidants in the Pathogenesis of Atherosclerosis: Implications for the Oxidized Low Density Lipoprotein Hypothesis, Atherosclerosis, 1998, p. 1-15, 141, Elsevier Science Ireland Ltd.
Patterson, Cam et al., The Oxidative Paradox: Another Piece in the Puzzle, Circulation Research, 2000, p. 1074-1076, 87, American Heart Association, United States.
Cai, Hua et al., Endothelial Dysfunction in Cardiovascular Diseases: the Role of Oxidant Stress, Circulation Research, 2000, p. 840-844, 87, American Heart Association, United States.

Solov'Eva Eiu et al., Zh Nevrol Psikhiatr Im S S Korsakova, 2008, p. 37-42, 108(6).
Hamilton, Carlene A. et al., Strategies to Reduce Oxidative Stress in Cardiovascular Disease, Clinical Science, 2004, p. 219-234, 106, The Biochemical Society, Great Britain.
Teng, Che-Ming et al., Vasoconstricting Effect in Rat Aorta caused by Thaliporphine Isolated from the Plant Nelistsea Konishii K, European Journal of Pharmacology, 1993, p. 7-12, 233, Elsevier Science Publishers.
Su, Ming-Jai et al., Thaliporphine, a Positive Inotropic Agent with a Negative Chronotropic Action, European Journal of Pharmacology, 1994, p. 141-150, 254, Elsevier Science.
Chiao, Chin-Wei et al., Thaliporphine Increases Survival Rate and Attenuates Multiple Organ Injury in LPS-Induced Endotoxaemia, Naunyn-Schmiedeberg's Arch Pharmacol, 2005, p. 34-43, 371, Springer-Verlag.
Ubeda, Amalia et al., Iron-Reducing and Free-Radical-Scavenging Properties of Apomorphine and Some Related Benzylisoquinolines, Free Radical Biology & Medicine, 1993, p. 159-167, 15, Pergamon Press Ltd., United States.
Chi, Tzong-Cherng et al., Antihyperglycemic Effect of Aporphines and their Derivatives in Normal and Diabetic Rats, Planta Med, 2006, p. 1175-1180, 72, Georg Thieme Verlag Kg Stuttgart, New York.
Mason, Justin C., Statins and their Role in Vascular Protection, Clinical Science, 2003, p. 216-266, 105, The Biochemical Society, Great Britain.
Shao, Jing et al., Receptor-Independent Intracellular Radical Scavenging Activity of an Angiotensin II Receptor Blocker, Journal of Hypertension, 2007, p. 1643-1649, 25, Lippincott Williams & Wilkins.
Wenzel, Philip et al., AT1-Receptor Blockade by Telmisartan Upregulates GTP-Cyclohydrolase I and Protects eNOS in Diabetic Rats, Free Radical Biology & Medicine, 2008, p. 619-626, 45, Elsevier Inc.
Kobayashi, Naohiko et al., Cardioprotective Mechanism of Telmisartan via PPAR-γ-eNOS Pathway in Dahl Salt-Sensitive Hypersensitive Rats, American Journal of Hypertension, May 2008, p. 576-581, vol. 21, No. 5.
Bertrand, Michel E., Provision of Cardiovascular Protection by ACE Inhibitors: a Review of Recent Trials, Current Medical Research and Opinion, Oct. 2004, p. 1559-1569, vol. 20, No. 10, Librapharm Limited.
Fu, Yun-Feng et al., Captopril Restores Endothelium-Dependent Relaxation of Rat Aortic Rings after Exposure to Homocysteine, J Cardiovasc Pharmacol, Oct. 2003, p. 566-572, vol. 42, No. 4, Lippincott Williams & Wilkins.
Liu, Yu-Hui et al., Impairment of Endothelium-Dependent Relaxation of Rat Aortas by Homocysteine Thiolactone and Attenuation by Captopril, J Cardiovasc Pharmacol, Aug. 2007, p. 155-161, vol. 50, No. 2, Lippincott Williams & Wilkins.
Frits H. A. F. De Man et al., Normal Oxidative Stress and Enhanced Lipoprotein Resistance to In Vitro Oxidation in Hypertriglyceridemia: Effects of Bezafibrate Therapy, Arteriosclerosis, Thrombosis, and Vascular Biology, 2000, p. 2434-2440, 20.

(Continued)

*Primary Examiner* — Charanjit Aulakh
(74) *Attorney, Agent, or Firm* — Hsiu-Ming Saunders; Intellectual Property Connections, Inc.

(57) ABSTRACT

The present invention discloses novel pharmaceutically acceptable salts of aporphine compounds and carboxyl-group containing agents. Also, the present invention discloses methods for preparing the pharmaceutically acceptable salts. These pharmaceutically acceptable salts are suitable for use in treating and/or preventing hyperglycemic disease and/or several oxidative stress related diseases.

19 Claims, 10 Drawing Sheets

OTHER PUBLICATIONS

Black C et al., Meglitinide Analogues for Type 2 Diabetes Mellitus (Review), The Cochrane Collaboration, 2007, 2, John Wiley & Sons, Ltd.

Blicklé, JF, Meglitinide Analogues: A Review of Clinical Data Focused on Recent Trials, Diabetes Metab, 2006, p. 113-120, 32.

Manzella, Daniela et al., Oral Amino Acid Administration Decreases Oxidative Stress and Improves Brachial Reactivity in Elderly Individuals, American Journal of Hypertension, Ltd., 2005, p. 858-863, 18.

Pisarenko, Oleg I, Mechanisms of Myocardial Protection by Amino Acids: Facts and Hypotheses, Clinical and Experimental Pharmacology, 1996, p. 627-633, 23.

Arsenian, Michael, Potential Cardiovascular Applications of Glutamate, Aspartate, and Other Amino Acids, Clin. Cardiol., 1998, p. 620-624, 21.

Xu, Yan-Jun et al., The Potential Health Benefits of Taurine in Cardiovascular Disease, Experimental Cardiology: Review, 2008, p. 57-65, vol. 13, No. 8, Pulsus Group Inc.

Oudit, Gavin Y. et al., Taurine Supplementation Reduces Oxidative Stress and Improves Cardiovascular Function in an Iron-Overload Murine Model, Circulation, 2004, p. 1877-1885, 109, American Heart Association.

Lass, Achim et al, Functional and Analytical Evidence for Scavenging of Oxygen Radicals by L-Arginine, Molecular Pharmacology, 2002, p. 1081-1088, vol. 61, No. 5, The American Society for Pharmacology and Experimental Therapeutics.

Huynh, Ngan Ngoc et al., Amino Acids, Arginase and Nitric Oxide in Vascular Health, Clinical and Experimental Pharmacology and Physiology, 2006, p. 1-8, 33, Blackwell Publishing Asia Pty Ltd.

Alabovsky, V. V. et al, Effect of Histidine-Containing Dipeptides on Isolated Heart under Ischemia/Reperfusion, Biochemistry (Moscow), 1997, p. 77-87, vol. 62, No. 1.

Soobrattee, M. A. et al, Phenolics as Potential Antioxidant Therapeutic Agents: Mechanism and Actions, Mutation Research, 2005, p. 200-213, 579, Elsevier B.V.

Kata, Atsushi et al., Inhibitory Effects of Zingiber Officinale Roscoe Derived Components on Aldose Reductase Activity in Vitro and in Vivo, Journal of Agricultural and Food Chemistry, 2006, p. 6640-6644, 54, American Chemical Society.

Marquez, R., et al., Cyanoside Chloride and Chromocarbe Diethylamine are More Effective than Vitamin C against Exercise-Induced Oxidative Stress, Pharmocology & Toxicology, 2001, 89, p. 255-258.

\* cited by examiner

PHARMACEUTICALLY ACCEPTABLE SALTS OF APORPHINE DERIVATIVES AND CARBOXYL GROUP-CONTAINING AGENTS AND METHODS FOR PREPARING THE SAME

CROSS-REFERENCE TO RELATED APPLICATION

This application claims the benefit of the filing date of U.S. Provisional Application Ser. No. 61/074,246, entitled "APORPHINE DERIVATIVES, APORPHINE DERIVATIVES SALTS AND THEIR PHARMACEUTICAL USES" filed Jun. 20, 2008 under 35 USC & 119(e)(1).

BACKGROUND OF THE INVENTION

1. Field of the Invention

The present invention relates to some novel salts of aporphine compounds and methods for preparing the same and, more particularly, to pharmaceutically acceptable salts of aporphine compounds and carboxyl-group containing agents and methods for preparing the same.

2. Description of Related Art

A multitude of studies in experimental animals, together with clinical data, provide evidence that increased production of ROS (reactive oxygen species) are involved in the development and progression of cardiovascular disease including atherogenesis. In particular, the paper demonstrates various steps where oxidative stress could be involved in atherogenesis (Chen J et al., *Indian Heart J* 2004; 56: 163-173). Atherosclerosis is the buildup of fatty deposits called plaque on the inside walls of arteries. Arteries are blood vessels that carry oxygen and blood to the heart, brain, and other parts of the body. As plaque builds up in an artery, the artery gradually narrows and can become clogged. As an artery becomes more and more narrowed, less blood can flow through.

Oxidative stress refers to the physico-chemical, chemical, biochemical and toxicological behavior of the Reactive Oxygen Species (ROS). Oxidative stress plays a significant role in the pathogenesis of atherosclerosis and its complications. Oxidative stress mediates cell damage, in part, via reactive oxygen species (ROS). Oxidative stress has been identified throughout the process of atherogenesis. As the process of atherogenesis proceeds, inflammatory cells, as well as other constituents of the atherosclerotic plaque release large amounts of ROS, which further facilitate atherogenesis. In general, increased production of ROS may affect four fundamental mechanisms that contribute to atherosclerosis: endothelial cell dysfunction, vascular smooth muscle cells (VSMC) growth, monocyte migration and oxidation of low density lipoproteins (LDLs) (Alexander R W, *Hypertension* 1995; 25(2): 155-161; Berliner J A et al., *Free Radic Biol Med* 1996, 20: 707-727). A number of studies suggest that ROS oxidatively modified LDL is a more potent proatherosclerotic mediator than the native unmodified LDL (Heinecke J W., *Atherosclerosis* 1998, 141: 1-15). An important characteristic of endothelial dysfunction is impaired synthesis, release, and activity of endothelium-derived Nitric Oxide (NO). Nitric Oxide Synthase (NOS) converts Arginine into NO, the molecule that resists plaque formation, vasospasm, and abnormal clotting. Several studies have demonstrated that endothelial NO inhibits several processes involved in atherogenesis. For example, it mediates vascular relaxation and inhibits platelet aggregation, vascular SMC proliferation, and endothelium-leukocyte interactions. Inactivation of NO by superoxide anion limits the bioavailability of NO and leads to nitrate tolerance, vasoconstriction, and hypertension as well as atherosclerosis. Accordingly, if you can make and maintain Nitric Oxide then you will not develop cardiovascular disease. If the Nitric Oxide system can be successfully rebooted, then the cardiovascular disease can be stabilized.

ROS are involved in intracellular signalling. However, when ROS production is enhanced, dysregulation of physiological processes occurs. $O_2^-$ and other radicals may react with NO and cause endothelial dysfunction. The reaction of $O_2^-$ by NO leads to production of peroxynitrite. Peroxynitrite is itself a potent oxidant which can induce oxidation of proteins, lipids and DNA. In addition, ROS can stimulate vascular smooth muscle cell hypertrophy and hyperplasia. Furthermore, elevations in the levels of ROS may, via a variety of mechanisms, initiate development of a vascular pro-inflammatory state. This pro-inflammatory state may be promoted via activation of redox-sensitive transcription factors, such as nuclear factor B, the leucocyte adhesion molecule and vascular cell adhesion molecule 1, by reduction in levels of NO or by Angiotension-II-dependent pathways. Besides, risk factors for atherosclerosis, such as hypertension and hyperlipidemia, are also associated with increased generation of ROS (Patterson C et al., *Circ. Res.* 2000; 87(12): 1074-1076).

Oxidative stress alters many functions of the endothelium. As known in the art, oxidative stress is involved in the pathogenesis of a group of many diseases, such as cardiovascular diseases, including hypercholesterolemia, atherosclerosis, hypertension, diabetes, and heart failure etc. (Cai H et al., *Circ Res.* 2000; 87: 840-844), and ischemic cerebral diseases, including ischemic cerebral thrombosis, ischemic cerebral embolism, hypoxic ischemic encephalopathy etc. Department of Physiological Science, University of California also published that oxidative stress is thought to play a major role in the pathogenesis of a variety of human diseases, including atherosclerosis, diabetes, hypertension, aging, Alzheimer's disease, kidney disease and cancer (Roberts C K et al., *Life Sci.* 2009 Mar. 9). In addition, a role of the free-radical processes and disturbances of oxidative-restorative blood homeostasis and nervous tissue in the pathogenesis of brain ischemic pathology and other diseases was published (Solov'eva EIu et al., *Zh Nevrol Psikhiatr Im SS Korsakova.* 2008; 108(6): 37-42).

As ROS appear to have a critical role in many diseases, there has been considerable interest in identifying the enzyme systems involved and in developing strategies to reduce oxidative stress. Superoxide dismutase mimetics, thiols, xanthine oxidase and NAD(P)H (nicotinamide adenine dinucleotide phosphate reduced form) oxidase inhibitors are currently receiving much interest, while animal studies using gene therapy show promise, but are still at an early stage. Of the drugs in common clinical use, there is evidence that ACE (angiotensin-converting enzyme) inhibitors and $AT_1$(angiotensin II type 1) receptor blockers have beneficial effects on oxidative stress above their antihypertensive properties, whereas statins, in addition to improving lipid profiles, may also lower oxidative stress (Hamilton C A et al., *Clinical Science* 2004; 106. 219-234).

Meanwhile, for some aporphine derivatives, the effect on oxidative stress has been investigated. Hereafter, some known aporphine derivatives (e.g. thaliporphine, glaucine, N-[2-(2-methoxyphenoxy)ethyl]norglaucine) will be introduced.

Thaliporphine is an aporphine derivative, which is a phenolic alkaloid isolated from the plants of Neolitsea konishii K (Teng C M et al., *Eur J Pharmacol.* 1993, 233(1). 7-12). It has been disclosed that thaliporphine is a positive inotropic agent with a negative chronotropic action. This compound has antiarrhythmic action. (Su M J et al., *Eur. J Pharmacol.* 1994; 254: 141-150).

In ischemia or ischemia-reperfusion (I/R), nitric oxide (NO) can potentially exert several beneficial effects. Thaliporphine increased NO levels and exerted cardioprotective action in ischemic or I/R rats. Thaliporphine treatment significantly increased NO and decreased lactate dehydrogenase (LDH) levels in the blood during the end period of ischemia or I/R. These changes in NO and LDH levels by thaliporphine were associated with a reduction in the incidence and duration of ventricular tachycardia (VT) and ventricular fibrillation (VF) during ischemic or I/R period. Thaliporphine, acting via NO-dependent or NO-independent mechanisms, reduces ischemia or I/R-induced cardiac injury.

Thaliporphine could be a novel agent for attenuating endotoxin-induced circulatory failure and multiple organ injury and may increase the survival rate. These beneficial effects of thaliporphine may be attributed to the suppression of TNF-alpha (Tumor necrosis factor alpha), NO and superoxide anion ($O_2^-$) (Chiao C W et al., *Naunyn Schmiedebergs Arch Pharmacol.* 2005; 371(1): 34-43).

The vasorelaxant effect of glaucine was studied. Glaucine has an intracellular effect and also acts on the cell membrane by blocking voltage-dependent and receptor-operated calcium channels (Loza I, *Planta Med.* 1993, 59(3): 229-231). The scavenging and iron-reducing properties of a series of benzylisoquinolines of natural and synthetic origin have been studied. Boldine and glaucine acted as scavengers of hydroxyl radical in the deoxyribose degradation by $Fe^{3+}$-EDTA +$H_2O_2$ (Fenton's reagent) (Ubeda A et al., *Free Radic Biol Med.* 1993; 15(2): 159-167).

The antihyperglycemic actions of some aporphines and their derivatives in normal Wistar, streptozotocin (STZ)-induced diabetic (IDDM, Insulin-dependent diabetes mellitus) and nicotinamide-STZ induced diabetic (NIDDM, Non-insulin-dependent diabetes mellitus) rats were investigated. These compounds included thaliporphine, glaucine, boldine, and the derivatives, N-[2-(2-methoxyphenoxy)ethyl]norglaucine and diacetyl-N-allylsecoboldine. Thaliporphine exerts an antihyperglycemic action through insulin-dependent and insulin-independent mechanisms. Glaucine and boldine exerted less potent hypoglycemic action in STZ-diabetic rats. Both compounds may lower the plasma glucose mainly through an insulin-dependent mechanism. N-methyllaurotetanine and predicentrine produce their antihyperglycemic effect through an insulin-independent mechanism (Chi T C et al. *Planta Med.* 2006; 72(13): 1175-1180).

U.S. Pat. No. 6,313,134 discloses thaliporphine and its derivatives for the treatment and/or prophylaxis of cardiac diseases, including cardiac arrhythmia, myocardial ischemia or myocardial infarction, and sudden death caused by cardiac arrhythmia or acute myocardial infarction.

U.S. Pat. No. 7,057,044 provides aporphine and oxoaporphine compounds that have endothelial nitric oxide synthase (eNOS) maintaining or enhancing activities and may be used to manufacture a medicaments for preventing or treating ischemic diseases in human and mammal, and the ischemic diseases may include ischemic cerebral apoplexy, ischemic cerebral thrombosis, ischemic cerebral embolism, hypoxic ischemic encephalopathy, ischemic cardiac disease or ischemic enteropathy etc.

Aporphine and thaliporphine derivatives have the antihyperglycemic activities. Aporphine and thaliporphine derivatives may be used to prevent or treat hyperglycemic disease in human and mammal.

In addition to aporphine derivatives, some known carboxyl group-containing agents having effects on oxidative stress were disclosed as follows.

[Statins]

(a) Cardioprotective Actions of Statins

Statins increase NO bioavailability through PI3K/Akt (Phosphatidylinositol 3-kinase/Akt) and Rho-mediated signaling. NO can then mediate cytoprotection in the setting of myocardial ischemia and reperfusion through effects on the coronary vasculature and at the level of the mitochondria within cardiac myocytes. The vascular effects of increased NO bioavailability include the attenuation of both platelet and leukocyte adhesion and plugging within the coronary microcirculation and coronary vasodilatation. Statin-mediated generation of NO can also result in protection of the mitochondria through the activation of mitochondrial $K_{ATP}$ ($mK_{ATP}$) channels. The opening of these channels serves to depolarize the mitochondrial membrane, maintain the integrity of the mitochondrial matrix and decrease ROS generation by the mitochondria following ischemia and reperfusion. With statins, a class of compounds is intended, comprising as main components fluvastatin, pravastatin, atorvastatin, cerivastatin, rosuvastatin, pitavastatin, lovastatin acid and simvastatin acid.

(b) Statins and Their Role in Vascular Protection

The statins reduce cholesterol synthesis through inhibition of HMG-CoA (3-hydroxy-3-methylglutaryl-CoA) reductase and are widely prescribed for hyperlipidaemia to reduce the risk of atherosclerotic complications. The beneficial effect of lipid lowering by statins in the treatment of coronary heart disease has been demonstrated in large clinical trials. However, statins appear to have additional benefits on vascular function above and beyond their lipid lowering effects. Through inhibition of L-mevalonate synthesis, statins also prevent the synthesis of isoprenoid intermediates, including farnesylpyrophosphate and geranylgeranylpyrophosphate. Isoprenylation is important in the post-translational modification of a variety of proteins, including the small GTPases Rho, Rac and Ras, and hence plays an integral role in cellular signalling. Moreover, interference with isoprenylation underlies many of the beneficial actions of the statins on vascular endothelium, which include increased endothelial nitric oxide synthase expression, pro-angiogenic effects, increased fibrinolytic activity, immunomodulatory and anti-inflammatory actions, including increased resistance to complement. (Mason J C., *Clinical Science* 2003, 105: 251-266).

(c) Statins and Their Role in NO:

NO plays a central role in the maintenance of normal endothelial function and is generated in response to laminar shear stress. Endothelial NO is a vasodilator, inhibits smooth muscle proliferation, platelet aggregation, endothelial adhesion molecule expression and leucocyte-EC interactions. The demonstration that statins are able to enhance local NO generation in ECs, by increasing the half-life of eNOS (endothelial NO synthase) mRNA, was fundamental to the acceptance of the emerging evidence for lipid-independent effects. Statins retain their ability to increase eNOS in the presence of oxidized LDL and under hypoxic conditions. In addition, statins exert further beneficial effects on the endothelium through their inhibition of the expression of the potent vasoconstrictor endothelin-1. These actions have now been demonstrated for a number of different statins, including simvastatin, lovastatin, atorvastatin, pravastatin and fluvastatin in vivo and in vitro studies (Mason J C., *Clinical Science* 2003; 105: 251-266).

Atherosclerosis induced an endothelial [NO]/[ONOO$^-$] balance indicative of endothelial dysfunction. Statins showed anti-atherosclerotic effects mediated by $HO^{-1}$/eNOS, restoring the [NO]/[ONO O$^-$] imbalance and reducing lipid peroxidation.

[Angiotensin II Receptor Blockers]

(a) Application of Angiotensin II Receptor Blockers

Angiotensin II receptor blockers (ARBs) can be employed for treating high blood pressure, and may be useful in the treatment of other cardiac diseases such as stroke, heart attack and congestive heart failure, and also seem to have a beneficial effect on the kidney, particularly the kidneys of people with diabetes.

Hypertension is an important risk factor in atherogenesis. There is activation of renin angiotensin system (RAS) in many hypertensive patients. Activation of RAS with the formation of angiotensin II (Ang II) and subsequent activation of Ang II receptors, mainly type I receptors (AT1R), has been implicated in atherogenesis. Ang II can exert multiple pro-atherogenic effects on vascular endothelial cells and smooth muscle cells(SMCs) by activating AT1R. Ang II enhances the uptake of ox-LDL and the biosynthesis of cholesterol in macrophages, leading to formation of foam cells; Ang II upregulates LOX-1 (lectin-like oxidized low-density lipoprotein receptor-1) gene and protein expression in cultured human coronary artery endothelial cells, and enhances the noxious effects of ox-LDL, both via AT1R activation. Ang II induces apoptosis of human coronary artery endothelial cells.

With angiotensin II receptor blockers (ARBs), a class of compounds is intended, comprising as main components losartan, valsartan, irbesartan, candesartan, telmisartan and olmesartan. Valsartan, candesartan and telmisartan are containing a carboxylic acid side chain. The pharmaceutical compositions containing them can be used as blood pressure-reducing drugs to treat and/or prevent stroke, heart attack and congestive heart failure and other cardiac diseases as cardiac arrhythmia, myocardial ischemia or myocardial infarction.

Ang II plays a crucial role in the induction of oxidative stress and the pathogenesis of cardiovascular and renal diseases, and the beneficial mechanisms of ARBs are multifactorial. (Shao J et al., *J Hypertens*. 2007; 25(8): 1643-1649.)

Telmisartan attenuated the oxidative stress induced by hydrogen peroxide in both cells, suggesting that it acted via a receptor-independent antioxidant effect. Telmisartan did not change expression levels of antioxidative enzymes such as catalase or glutathione peroxidase. Telmisartan inhibits intracellular oxidative stress, at least in part, in a receptor-independent manner, possibly owing to its lipophilic and antioxidant structure.

Several enzymatic sources of reactive oxygen species (ROS) were described as potential reasons of eNOS uncoupling in diabetes mellitus. Telmisartan inhibits activation of superoxide sources like NADPH oxidase, mitochondria, and xanthine oxidase. These effects may explain the beneficial effects of telmisartan on endothelial dysfunction in diabetes. (Wenzel P et al., *Free Radic Biol Med*. 2008, 45(5): 619-626.)

Cardioprotective mechanism of telmisartan is via PPAR-gamma-eNOS pathway in dahl salt-sensitive hypertensive rats. (Kobayashi N et al., *Am J Hypertens*. 2008; 21(5): 576-581) Telmisartan is a partial agonist of the peroxisome proliferator-activated receptor-gamma (PPAR-gamma). The cardioprotective mechanism of telmisartan may be partly due to improvement of endothelial function associated with PPAR-gamma-eNOS, oxidative stress, and Rho-kinase pathway.

[Angiotensin I Converting Enzyme Inhibitors]

(a) Application of Angiotensin I Converting Enzyme Inhibitors (ACEIs)

ACEIs are useful in the treatment of cardiovascular disorders, especially hypertension and congestive heart failure as well as for achieving other therapeutic effects by inhibiting the conversion of angiotensin I to angiotensin II.

With angiotensin I converting enzyme inhibitors, a class of compounds is intended, comprising as main components captopril, perindopri, ramipril, enalapril, fosinopril, quinapril, lisinopril, benazepril. The pharmaceutical compositions containing them are used for controlling blood pressure, treating heart failure and preventing kidney damage in people with hypertension or diabetes. They also benefit patients who have had heart attacks.

(b) Angiotensin I Converting Enzyme Inhibitors (ACEIs) and Their Role in Oxidative Stress and Cardiovascular Diseases ACEI improve the vasoconstrictive/vasodilatory balance by blocking the formation of angiotensin II and preventing the degradation of bradykinin. In vitro, animal and human experimental studies have shown that ACEI have several properties: promote vasodilation, limit neurohormonal activation and vasoconstriction during ischemia, improve endothelial function by reducing oxidative stress, and slow down the development of atherosclerosis. Previous trials have shown that ACEI reduced cardiovascular events in patients with heart failure or ventricular dysfunction. In PROGRESS (n=6105), a perindopril-based regimen reduced recurrent stroke by 28% and substantially reduced cardiac outcomes among individuals with cerebrovascular disease. In HOPE (n=9297), ramipril reduced the composite outcome (cardiovascular death, myocardial infarction and cerebrovascular accident) by 22% in patients with high cardiovascular risk. (Bertrand M E., *Curr Med Res Opin*. 2004; 20(10):1559-69.)

Captopril has protective effects against damages of vascular endothelium induced by homocysteine and lysophosphatidylcholine. Captopril can prevent the inhibition of endothelium-dependent relaxation induced by homocysteine in isolated rat aorta, which may be related to scavenging oxygen free radicals and enhancing NO production (Fu Y F et al., *J Cardiovasc Pharmacol*. 2003, 42(4): 566-572).

The mechanisms of endothelial dysfunction induced by homocysteine thiolactone (HTL) may include the decrease of NO and the generation of oxygen free radicals and that captopril can restore the inhibition of endothelium-dependent relaxation (EDR) induced by HTL in isolated rat aorta, which may be related to scavenging oxygen free radicals and may be sulfhydryl-dependent (Liu Y H et al., *J Cardiovasc Pharmacol*. 2007; 50(2): 155-161).

Formation of homocysteine (Hcy) is the constitutive process of gene methylation. The accumulation of homocysteine (Hcy) leads to increased cellular oxidative stress in which mitochondrial thioredoxin, and peroxiredoxin are decreased and NADH oxidase activity is increased.

Hyperhomocysteinaemia is an independent risk factor for atherosclerosis, including cardiovascular (CV) disease, cerebrovascular disease and peripheral vascular disease in the general population. The homocysteine theory of atherosclerosis was first suggested by McCully in 1969, following his observation that children with homocysteinuria and markedly elevated plasma homocysteine levels (>100 μmol/L) had severe premature arterial disease. Since then, many clinical and epidemiological studies have demonstrated that a mild or moderate increase in plasma homocysteine is a risk factor for vascular disease.

The adverse effects of homocysteine on endothelial function may be mediated by reduced production and bioavailability of nitric oxide due to oxidative stress. Hyperhomocysteinaemia could cause oxidative stress via a number of mechanisms. In vitro studies using cultured endothelial cells have demonstrated auto-oxidation of homocysteine to form reactive oxygen species, including superoxide anion and hydrogen peroxide, increased lipid peroxidation and impaired production of the antioxidant glutathione peroxidase.

[Fibric Acids]

(a) Application of Fibric Acids

Coronary heart disease patients with low high-density lipoprotein cholesterol (HDL-C) levels, high triglyceride levels, or both are at an increased risk of cardiovascular events.

Fibric acid derivatives effectively lower triglycerides and raise high-density lipoprotein (HDL) cholesterol, but their effect on low-density lipoprotein (LDL) cholesterol is weakly beneficial (small decreases) to adverse (small increases) and varies according to the triglyceride level. With fibric acid, a class of compounds is intended, comprising as main components bezafibrate, clofibric acid, fenofibric acid and gemfibrozil.

(b) Fibric cids and Their Role in Oxidative Stress and Cardiovascular Diseases

The Bezafibrate Infarction Prevention (BIP) study was another randomized, placebo-controlled trial studying the effects of bezafibrate among men and women with coronary heart disease (CHD) (*Circulation* 2000; 102: 21-27). Bezafibrate therapy demonstrated significant reductions in triglyceride and LDL concentrations and fibrinogen while elevating HDL levels. When the study was completed, bezafibrate was associated with a 9% reduction (p=0.26) in fatal and nonfatal myocardial infarction and sudden death. Overall mortality rates and frequency of newly diagnosed cancer were similar among the groups, showing bezafibrate to be safe agent among adults with CHD, but it had no significant effect on the frequency of major coronary events.

Although there is evidence that hyperlipidemia and predominance of small dense low density lipoproteins (LDLs) are associated with increased oxidative stress, the oxidation status in patients with hypertriglyceridemia (HTG) has not been studied in detail. Bezafibrate reversed the oxidation resistance to the normal range. In conclusion, these results indicate the following: (1) Hypertriglyceridemia is associated with normal in vivo oxidative stress and enhanced ex vivo resistance of lipoproteins to oxidation. (2) Bezafibrate reduces the resistance of lipoproteins to copper-induced oxidation and enhances oxidative stress in hypertriglyceridemia patients (*Arteriosclerosis, Thrombosis, and Vascular Biology*. 2000, 20: 2434-2440).

[Meglitinides]

(a) Application of Meglitinides

In type 2 diabetes mellitus, impairment of insulin secretion is an important component of the disease. The meglitinide analogues ("meglitinides") are a class of oral antidiabetic agents that increase insulin secretion in the pancreas. The properties of this class of drug suggest that they have the potential to produce a rapid, short-lived insulin output. With meglitinide, a class of compounds is intended, comprising as main components repaglinide, nateglinide and mitiglinide. Two analogues are currently available for clinical use: repaglinide and nateglinide (*Cochrane Database Syst Rev.* 2007; 18(2): CD004654).

(b) Meglitinides and Their Role in Cardiovascular Protection

Glinides (meglitinides) represent a chemically heterogeneous new class of insulin-secreting agents characterized by a rapid onset and short duration of action. They act by closure of the ATP-dependant K channel. Repaglinide has an equivalent HbA1c lowering effect to conventional sulfonylureas but reduces predominantly postprandial glucose levels. Nateglinide has an even shorter duration of action and has almost no effect on fasting plasma glucose levels. Several experimental data suggest that glinides could preserve B cell function over time better than hypoglycaemic sulfonylureas, and that the improvement of post-prandial glucose levels could exert a long term protective cardiovascular effect (*Diabetes Metab.* 2006; 32(2): 113-120].

[Other Carboxyl Group-Containing Agents]

Other Carboxyl Group-Containing Agents and Their Role in Oxidative Stress and Induced Diseases Atherosclerosis is a major cause of death in elderly individuals. Endothelial dysfunction is recognized as a key early event in atherogenesis. Administration of essential amino acids may improve brachial reactivity in elderly persons and may also protect against the development of atherosclerosis via the rise in plasma-free IGF-1 levels. (Manzella D et al., *Am J Hypertens*. 2005; 18(6): 858-863.)

The antioxidant supplement, n-acetyl cysteine, is a sulfur-based amino acid needed to synthesize glutathione, a natural antioxidant enzyme produced in the body to fight free-radical attack. Without glutathione, your body immune system would be greatly compromised, and left with little defense against toxins and disease.

N-acetyl cysteine may be effective in the prevention and/or treatment of cancer, heavy metal poisoning, smoker cough, bronchitis, heart disease, cystic fibrosis, acetaminophen poisoning, and septic shock. Its detoxifying effects may also help enhance the benefits of regular exercise by protecting the body from oxidative stress.

Acetylcysteine is a precursor in the formation of the antioxidant glutathione in the body. The thiol (sulfhydryl) group confers antioxidant effects and is able to reduce free radicals. Recent studies suggest that high-dose N-acetylcysteine provides better protection from contrast-induced nephropathy, and the antioxidant properties of N-acetylcysteine may also provide cardiac protection. N-acetylcysteine-enhanced contrast medium reduces MI size and protects renal function in a pig model of ischemia and reperfusion. Thrombolysis after acute myocardial infarction may lead to a number of adverse effects (reperfusion injury) such as myocardial stunning, arrhythmias and even myocardial damage and extension of the infarct size. Some recent clinical studies have demonstrated that the intravenous infusion of N-acetylcysteine during thrombolysis was associated with a decrease in infarct size and better preservation of left ventricular function, probably due to antioxidant and free radical scavenger properties of N-acetylcysteine.

Methionine and cysteine enhance force of contraction by N-methylation of membrane phospholipids of the sarcolemma and sarcoplasmic reticulum. Methionine and, to a lesser extent, cysteine may reduce myocardial damage by oxygen radical species. (Pisarenko O I., *Clin Exp Pharmacol Physiol*. 1996; 23(8): 627-633.)

Amino acids (e.g. glutamate, aspartate), or keto acids (e.g. pyruvic acid, 2-ketoglutaric acid) have myocardial protective properties. Cardioplegic solutions rich in the hydrophilic, basic amino acids, glutamate and aspartate, or keto acids have enhanced myocardial preservation and left ventricular function. Several biochemical mechanisms exist by which certain amino acids may attenuate ischemic or reperfusion injury. Glutamate and aspartate may become preferred myocardial fuels in the setting of ischemia. They may also reduce myocardial ammonia production and reduce cytoplasmic lactate levels, thereby deinhibiting glycolysis. Some amino acids may become substrate for the citric acid cycle. Glutamate and aspartate also move reducing equivalents from cytoplasm to mitochondria where they are necessary for oxidative phosphorylation and energy generation. A rationale exists for the use of an amino acid-rich cardioplegia-like solution in myocardial infarction. (*Clin Cardiol*. 1998; 21(9): 620-624.)

Pyruvate cardioplegia solution may be used in any surgery where the heart must be arrested, but it is particularly useful in cardiopulmonary bypass surgery. Because the solution relies primarily upon pyruvate to protect the heart from damage during and immediately after arrest, other additives are not as necessary as with current cardioplegia solutions or are not necessary at all. (US Patent Appl. 20030124503) Taurine (2-aminoethanesulphonic acid), a sulphur-containing amino acid, is found in most mammalian tissues. Taurine was found to exhibit diverse biological actions, including protection against ischemia-reperfusion injury, modulation of intracellular calcium concentration, and antioxidant, antiatherogenic and blood pressure-lowering effects. There is a wealth of experimental information and some clinical evidence available in the literature suggesting that taurine could be of benefit in cardiovascular disease of different etiologies. (*Exp Clin Cardiol*. 2008; 13(2): 57-65.) Taurine reduces iron-mediated myocardial oxidative stress, preserves cardiovascular function, and improves survival in iron-overloaded mice. The role of taurine in protecting reduced glutathione levels provides an important mechanism by which oxidative stress-induced myocardial damage can be curtailed. (Oudit G Y et al., *Circulation*. 2004; 109(15): 1877-1885.)

L-Arginine, the substrate of nitric oxide synthase, is known to exert favorable effects in the prevention and treatment of cardiovascular diseases. In several conditions, including atherosclerosis and ischemia/reperfusion, where oxygen metabolites are thought to mediate endothelial and myocardial injury, L-arginine has protective effects. (Lass A et al., *Mol Pharmacol*. 2002, 61: 1081-1088.) Nitric oxide (NO) plays a fundamental role in the vasculature because of its diverse influence in vascular protection, including its well-reported antiproliferative, anti-inflammatory, antithrombotic and vasodilator effects. In many vascular disease states, NO production is reduced as a result of endothelial dysfunction, in part caused by a decrease in substrate (L-arginine) availability. L-Arginine supplementation in patients with vascular disease is well reported to benefit patients therapeutically because of its effect on both NO-dependent and -independent mechanisms. The role of L-methionine and homocystine and their effect on NO also play an influential role in the body. (Huynh N N et al., *Clin Exp Pharmacol Physiol*. 2006, 33(1-2): 1-8)

The ability of carnosine to suppress significantly the development of ischemic reperfusion contracture and to support the restoration of the contractile force during reperfusion were shown. At the same time, a decrease of myoglobin and nucleoside release from myocytes was observed, this indicating a membrane-protecting effect of carnosine. Heart muscle protection by acetylated derivatives of carnosine and anserine under ischemia correlates with the preferential localization of these compounds in high quantities in the myocardium. (Alabovsky V V et al., *Biochemistry (Mosc)*. 1997; 62(1): 77-87.)

Accumulating chemical, biochemical, clinical and epidemiological evidence supports the chemoprotective effects of phenolic antioxidants against oxidative stress-mediated disorders. The pharmacological actions of phenolic antioxidants stem mainly from their free radical scavenging and metal chelating properties as well as their effects on cell signaling pathways and on gene expression. (Soobrattee M A et al., *Mutat Res*. 2005; 579(1-2): 200-213.)

Scientific research has gradually verified the antidiabetic effects of ginger (Zingiber officinale Roscoe). Especially gingerols, which are the major components of ginger, are known to improve diabetes including the effect of enhancement against insulin-sensitivity. Aldose reductase inhibitors have considerable potential for the treatment of diabetes, without increased risk of hypoglycemia. The assay for aldose reductase inhibitors in ginger led to the isolation of five active compounds. 2-(4-hydroxy-3-methoxyphenyl)ethanoic acid, one carboxyl group-containing phenolic compound of the five active compounds, was a good inhibitor of recombinant human aldose reductase. These results suggested that it would contribute to the protection against or improvement of diabetic complications for a dietary supplement of ginger or its extract containing aldose reductase inhibitors. (Kato A et al., *J Agric. Food Chem*. 2006; 54(18): 6640-6644.)

Chromocarbe diethylamine is more effective than vitamin C against exercise-induced oxidative stress. Chromocarbe diethylamine was more effective than vitamin C in the prevention of glutathione oxidation in blood. Furthermore, chromocarbe diethylamine partially prevented muscle damage. Chromocarbe diethylamine was the most effective compound in the prevention of exercise-induced lipid peroxidation in plasma. (*Pharmacol Toxicol*. 2001; 89(5): 255-258.)

SUMMARY OF THE INVENTION

The object of the present invention is to provide a novel pharmaceutically acceptable compound, i.e. a salt of an aporphine derivative and a carboxyl group-containing agent, in which the aporphine derivative and the carboxyl group-containing agent have effects on oxidative stress.

To achieve the object, the present invention provides a pharmaceutically acceptable compound, which is a 1:1 salt of a basic group-containing compound represented by the following formula (I) and a carboxyl group-containing agent,

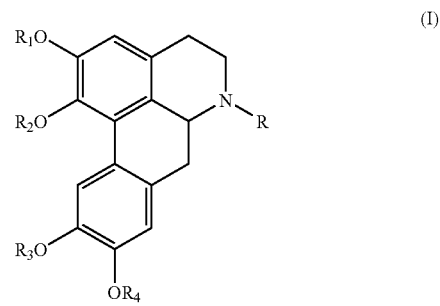

wherein, each of $R_1$, $R_2$, $R_3$ and $R_4$, independently, is hydrogen, $C_{1-6}$alkyl, or —C(O)$R_5$;

R is hydrogen, $C_{1-6}$ alkyl, —C(O)$R_5$, or $C_{1-6}$ alkyl substituted by the following group: —C(O)O$R_6$, —C(O)N$R_6R_7$, —O$R_6$, —N$R_6R_7$, $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl;

$R_5$ is $C_{4-9}$ heteroaryl containing at least one heteroatom selected from the group consisting of N, O and S, or $C_{1-6}$ alkyl substituted by —N$R_6R_7$ or $C_{4-9}$ heterocyclyl containing at least one heteroatom selected from the group consisting of N, O and S;

each of $R_6$ and $R_7$, independently, is hydrogen, $C_{1-6}$ alkyl, $C_{4-9}$ heteroaryl containing at least one heteroatom selected from the group consisting of N, O and S, $C_{4-9}$ heterocyclyl containing at least one heteroatom selected from the group consisting of N, O and S , or $C_{6-10}$ aryl unsubstituted or substituted by at least one selected from the group consisting of halogen, hydroxyl, $C_{1-6}$ alkoxy and $C_{1-6}$ alkyl; and the carboxyl group-containing agent is selected from the group consisting of a statin, an angiotensin II receptor blocker, an angiotensin I converting enzyme inhibitor, a fibric acid, a meglitinide, and a specific acid.

Accordingly, since the pharmaceutically acceptable compound according to the present invention contains two kinds of active agents (i.e. an aporphine derivative and a carboxyl group-containing agent), the pharmaceutically acceptable compound according to the present invention can exhibit synergistic pharmacological activities of the aporphine derivative and the carboxyl group-containing agent so as to achieve a better combined therapeutic effects.

With regard to the pharmaceutically acceptable compound of the present invention, since the aporphine derivative functions as a base and the carboxyl group-containing agent functions as an acid, the aporphine derivative and the carboxyl group-containing agent can react with each other to form a 1:1 salt (e.g. a statin salt of aporphine compound, an angiotensin II receptor blocker salt of aporphine compound, an angiotensin I converting enzyme inhibitor salt of aporphine compound, a fibric acid salt of aporphine compound, and a meglitinide salt of aporphine compound), which has unique characteristics distinguishable from either carboxyl group-containing agent alone or aporphine derivative alone, based on the testing results in Fourier-Transformed Infrared Spectroscopy (FTIR), LC/MS and NMR analyses. Additionally, the pharmaceutically acceptable compound of the present invention may be converted into the carboxyl group-containing agent and the aporphine compound in the body after administration.

Referring to Formula (I), preferably, each of $R_1$, $R_2$, $R_3$ and $R_4$, independently, is hydrogen or $C_{1-6}$ alkyl, and R is hydrogen, $C_{1-6}$ alkyl, —C(O)$R_5$, or $C_{1-6}$ alkyl substituted by —C(O)O$R_6$, —C(O)N$R_6R_7$, —O$R_6$ or $C_{4-9}$ heteroaryl containing at least one heteroatom selected from the group consisting of N, O and S.

Referring to Formula (I), more preferably, each of $R_1$, $R_2$, $R_3$ and $R_4$, independently, is hydrogen or $C_{1-6}$ alkyl, and R is hydrogen, $C_{1-6}$ alkyl, —C(O)$R_5$, or $C_{1-6}$ alkyl substituted by —C(O)O$R_6$, —C(O)N$R_6R_7$, $C_{4-9}$ heteroaryl containing at least one heteroatom selected from the group consisting of N, O and S, one —O$R_6$, or both of hydroxyl and —O—$C_{6-10}$ aryl unsubstituted or substituted by at least one selected from the group consisting of halogen, hydroxyl, $C_{1-6}$ alkoxy and $C_{1-6}$ alkyl.

Referring to Formula (I), most preferably, each of $R_1$, $R_2$, $R_3$ and $R_4$, independently, is hydrogen or $C_{1-6}$ alkyl, and R is hydrogen, $C_{1-6}$ alkyl, —C(O)$R_5$, or $C_{1-6}$ alkyl substituted by C(O)N$R_6R_7$, $C_{4-9}$ heteroaryl containing at least one heteroatom selected from the group consisting of N, O and S, one —O$R_6$, or both of hydroxyl and —O—$C_{6-10}$ aryl unsubstituted or substituted by at least one selected from the group consisting of halogen, hydroxyl, $C_{1-6}$ alkoxy and $C_{1-6}$ alkyl. Herein, preferably, $R_6$ is $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl, and $R_7$ is hydrogen.

Referring to Formula (I), specifically, R may be hydrogen, $C_{1-6}$ alkyl,

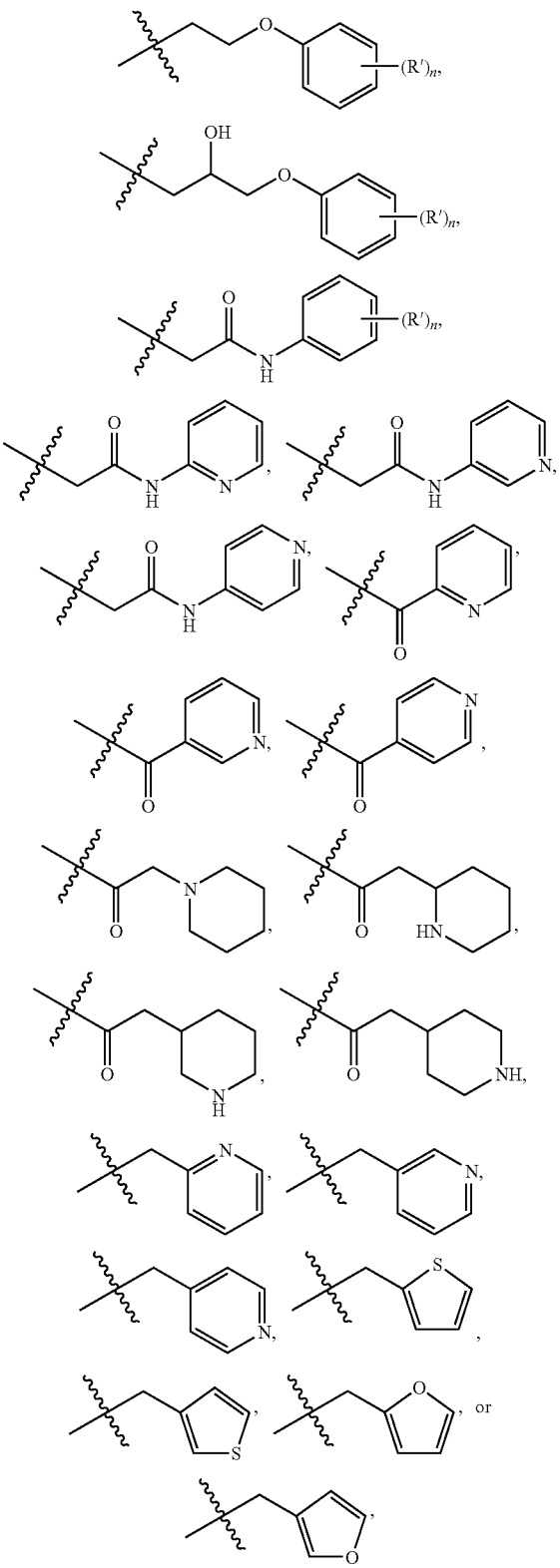

n being an integer from 0 to 5, and R' independently being halogen, hydroxyl, $C_{1-6}$ alkoxy or $C_{1-6}$ alkyl.

Exemplary compounds of the formula (I) are shown below.
| Compound No. | Structure |
|---|---|
| 1 | 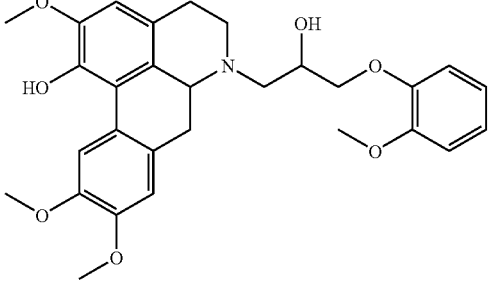 |
| 2 | 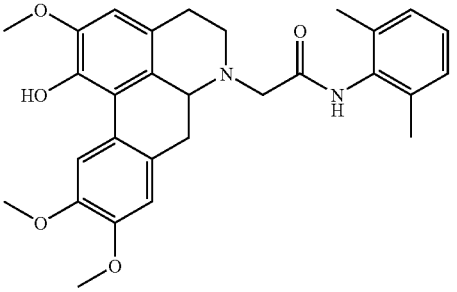 |
| 3 | 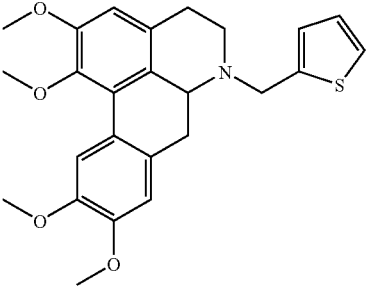 |
| 4 | 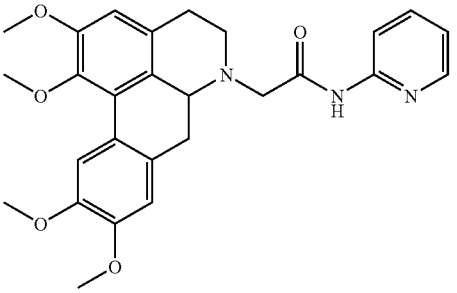 |
| 5 | 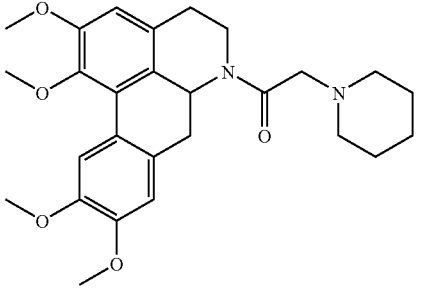 |
-continued
| Compound No. | Structure |
|---|---|
| 6 | 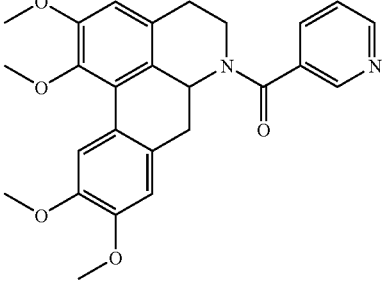 |
| 7 | 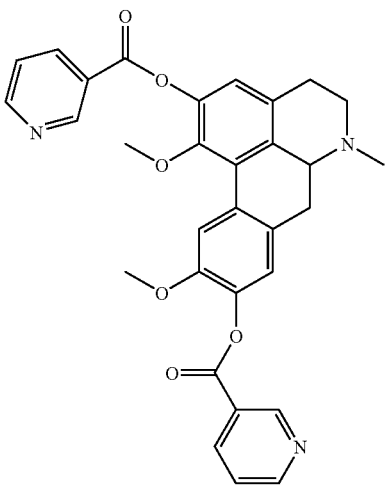 |
| 8 | 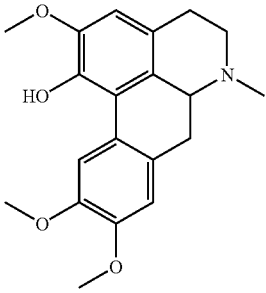 |
| 9 | 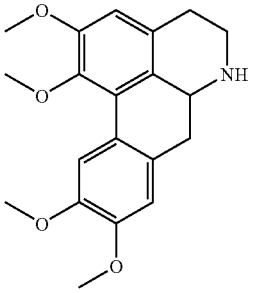 |

-continued

| Compound No. | Structure |
|---|---|
| 10 | 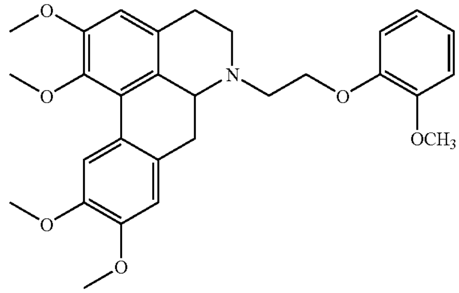 |
| 11 | 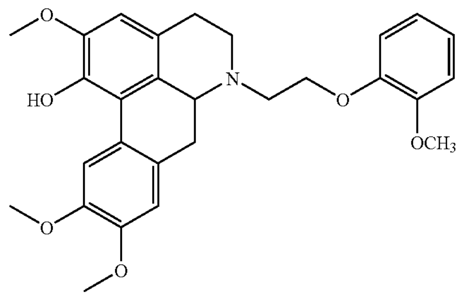 |

In the present invention, the term "alkyl" refers to a straight or branched hydrocarbon. Examples of alkyl include, but are not limited to, methyl, ethyl, n-propyl, i-propyl, n-butyl, i-butyl, and t-butyl.

In the present invention, the term "aryl" refers to a 6-carbon monocyclic, 10-carbon bicyclic aromatic ring system wherein each ring may have 1 to 4 substituents. Examples of aryl groups include, but are not limited to, phenyl and naphthyl.

In the present invention, the term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy.

In the present invention, the term "heteroaryl" refers to a hydrocarbon ring system (mono-cyclic or bi-cyclic) having at least one aromatic ring which contains at least one heteroatom such as O, N, or S as part of the ring system and the remainder being carbon. Examples of heteroaryl moieties include, but are not limited to, furyl, pyrrolyl, thienyl, oxazolyl, imidazolyl, thiazolyl, pyridinyl, pyrimidinyl, benzimidazolyl, benzothiazolyl, coumarinyl, quinazolinyl, and indolyl. In the present invention, the term "heterocyclyl" refers to a nonaromatic ring system having at least one heteroatoms (such as O, N, or S). Examples of heterocyclyl groups include, but are not limited to, piperidinyl, piperazinyl, pyrrolidinyl, dioxanyl, morpholinyl, and tetrahydrofuranyl.

According to the pharmaceutically acceptable compound of the present invention, preferably, the statin is selected from the group consisting of fluvastatin, pravastatin, atorvastatin, cerivastatin, rosuvastatin, pitavastatin, lovastatin acid and simvasatin acid. Until the present invention described herein, there was no report of a statin salt of aporphine compound. The statin salt of aporphine compound may achieve synergistic pharmacological activities. Statins can increase endothelial nitric oxide synthase expression on vascular endothelium. Aporphine compounds can inhibit lipid peroxidase, exert the free radical scavenging activities and protect vascular smooth muscle cells. The parts of the synergistic effects from aporphine compounds are lipid peroxidase inhibition, free radical scavenging activities, and vascular smooth muscle cells protection; and the other parts from statins are lowering-lipid effect, antioxidative effect, vascular protection and increase endothelial nitric oxide synthase expression. The above may make the statin salt of aporphine compound having better combined therapeutic effects in the preventing progression of atherosclerosis, cardiovascular protection and the prevention and treatment of coronary heart disease (CHD) events.

According to the pharmaceutically acceptable compound of the present invention, preferably, the angiotensin II receptor blocker is selected from the group consisting of valsartan, candesartan and telmisartan. Until the invention described herein, there was no report of angiotensin II receptor blocker (ARB) salt of aporphine compound. Angiotensin II receptor blocker salt of thaliporphine may achieve synergistic pharmacological activities. Angiotensin II receptor blockers can attenuate the oxidative stress and improve vascular function. Aporphine compounds can inhibit lipid peroxidase, exert the free radical scavenging activities and protect vascular smooth muscle cells. The parts of the synergistic effects from aporphine compounds are lipid peroxidase inhibition, free radical scavenging activities, and vascular smooth muscle cells protection; and the other parts from angiotensin II receptor blockers are antioxidative effect, lowering-hypertension effect, oxidative stress inhibition effect, endothelial nitric oxide synthase (eNOS) enhancing effect, and vascular function improvement. The above may make the angiotensin II receptor blocker salt of aporphine compound having better combined therapeutic effects in the preventing progression of atherosclerosis, cardiovascular protection and the prevention and treatment of coronary heart disease (CHD) events.

According to the pharmaceutically acceptable compound of the present invention, preferably, the angiotensin I converting enzyme inhibitor is selected from the group consisting of captopril, perindopril, ramipril, enalapril, fosinopril, quinapril, lisinopril and benazepril. Until the invention described herein, there was no report of Angiotensin I converting enzyme inhibitor (ACEI) salt of aporphine compound. Angiotensin I converting enzyme inhibitor salt of thaliporphine may achieve synergistic pharmacological activities. Angiotensin I converting enzyme inhibitors can protect against damages of vascular endothelium induced by homocysteine and scavenge oxygen free radicals. Aporphine compounds can inhibit lipid peroxidase, exert the free radical scavenging activities and protect vascular smooth muscle cells. The parts of the synergistic effects from aporphine compounds are lipid peroxidase inhibition, free radical scavenging activities, and vascular smooth muscle cells protection; and the other parts from angiotensin I converting enzyme inhibitors are antioxidative effect, lowering-hypertension effect, endothelial nitric oxide synthase (eNOS) enhancing effect, homocysteine inhibition effect and protection against damages of vascular endothelium. The above may make the angiotensin I converting enzyme inhibitor salt of aporphine compound having better combined therapeutic effects in the preventing progression of atherosclerosis, cardiovascular protection and the prevention and treatment of coronary heart disease (CHD) events.

According to the pharmaceutically acceptable compound of the present invention, preferably, the fibric acid is selected from the group consisting of bezafibrate, clofibric acid, fenofibric acid and gemfibrozil. Until the invention described herein, there was no report of fibric acid salt of aporphine compound. Fibric acid salt of aporphine compound may achieve synergistic pharmacological activities. Fibric acids can effectively lower triglycerides and reverse the oxidative stress. Aporphine compounds can inhibit lipid peroxidase, exert the free radical scavenging activities and protect vascular smooth muscle cells. The parts of the synergistic effects from aporphine compounds are lipid peroxidase inhibition, free radical scavenging activities, and vascular smooth muscle cells protection; and the other parts from fibric acids are antioxidative effect, lowering-triglyceride effect, endothelial nitric oxide synthase (eNOS) enhancing effect, and oxidative stress inhibition. The above may make the fibric acid salt of aporphine compound having better combined therapeutic effects in the preventing progression of atherosclerosis, cardiovascular protection and the prevention and treatment of coronary heart disease (CHD) events.

According to the pharmaceutically acceptable compound of the present invention, preferably, the meglitinide is selected from the group consisting of repaglinide, nateglinide and mitiglinide. Until the invention described herein, there was no report of meglitinide salt of aporphine compound. Meglitinide salt of aporphine may achieve synergistic pharmacological activities. Meglitinide can improvement of postprandial glucose levels. Aporphine compounds can also produce antihyperglycemic effect. The parts of the synergistic effects from aporphine compounds are lipid peroxidase inhibition, free radical scavenging activities, and vascular smooth muscle cells protection; and the other part from meglitinides is antihyperglycemic effect. The above may make the meglitinide salt of aporphine compound having better combined therapeutic effects in the preventing or treating hyperglycemic disease in human and mammal and cardiovascular protection.

According to the pharmaceutically acceptable compound of the present invention, preferably, the specific acid is selected from the group consisting of an amino acid, a phenolic acid, a chromocarb, an ozagrel, a capobenic acid, a pyruvic acid, a 2-ketoglutaric acid, a phosphocreatine, a thioctic acid, an acipimox, an ambrisentan, a tirofiban, an active metabolite of clopidogrel and an active metabolite of ticlopidine. Herein, the amino acid is one selected from the group consisting of a cysteine, an acetyl cysteine, a thioproline, a carnosine, a carnitine, a phosphoserine, a tiopronin, a methionine, a glutamine, a glutathione, a pyridoxal 5-phosphate, a nicotinic acid, a mono-arginine oxoglurate, a taurine and an orotic acid, and the phenolic acid is one selected from the group consisting of an acetyl salicylic acid, a salsalate, a caffeic acid, a ferulic acid, a p-hydroxyphenylacetic acid, a 4-hydroxy-3-methoxyphenylacetic acid, a p-coumaric acid, and a sinapic acid. For specific acid salt of aporphine, the parts of the synergistic effects from aporphine compounds are lipid peroxidase inhibition, free radical scavenging activities, and vascular smooth muscle cells protection; and parts from specific acids are antioxidative effect and endothelial nitric oxide synthase (eNOS) enhancing effect. The above may make the specific acid salt of aporphine having better combined therapeutic effects in the myocardial protection and the prevention and treatment of coronary heart disease (CHD) events.

Accordingly, the novel aporphine compound salts may be employed for treating and/or preventing hyperglycemic disease and several oxidative stress related diseases, such as coronary syndromes, neurodegenerative disorders, reducing cholesterol levels as well as may achieve other therapeutic effects, including treatment and/or prophylaxis of cardiac diseases, including cardiac arrhythmia, myocardial ischemia or myocardial infarction, and sudden death caused by cardiac arrhythmia or acute myocardial infarction and treatment of cardiovascular disorders, especially hypertension and congestive heart failure and preventing progression of coronary atherosclerosis, and treatment and/or prophylaxis of ischemic diseases, especially ischemic cerebral apoplexy, ischemic cerebral thrombosis, ischemic cerebral embolism, hypoxic ischemic encephalopathy, ischemic cardiac disease or ischemic enteropathy.

In the present invention, the pharmaceutically acceptable compound of the present invention can be administered by any suitable route including transnasal, topical, rectal, buccal, oral or parenteral. The pharmaceutically acceptable compound may be liquid or solid for topical, oral or parenteral administration in form of tablets, capsules and pills eventually with enteric coating, powders, granules, pellets, emulsions solutions, suspensions, syrups, elixir, ointments, creams, injectable forms or liposomes.

The present invention further provide a method for preparing the above-mentioned pharmaceutically acceptable compound, including the following steps: dissolving the basic group-containing compound of the formula (I) in a free base form or in a salt form and the carboxyl group-containing agent in a free acid form or in a salt form in a first solvent to form a solution; and removing the first solvent from the solution or mixing the solution with a second solvent to obtain the pharmaceutically acceptable compound.

In the method for preparing the pharmaceutically acceptable compound according to the present invention, the first solvent used might be any solvent in which the basic group-containing compound of the formula (I) and the carboxyl group-containing agent can be well dissolved, such as water, $C_{1-8}$ straight or branched alcohols, acetone, methyl ethyl ketone, methyl isobutyl ketone, dichloromethane, diethyl ether, diisopropyl ether, dimethyl sulfoxide, N,N'-dimethylformamide, N,N'-dimethylacetamide, and a mixture of the above-mentioned thereof. Additionally, the second solvent used might be any solvent, which is miscible with the first solvent and can cause the precipitation of the pharmaceutically acceptable compound, such as acetonitrile, ethanol, acetone, methyl ethyl ketone, dichloromethane, diethyl ether, diisopropyl ether, or the combination thereof.

In the method for preparing the pharmaceutically acceptable compound according to the present invention, any conventional methods that can be used to remove the solvent can be used for removing the solvent from the mixture. The preferred methods for removing the solvent include, but are not limited to, concentrated and crystallized by natural evaporation, vacuum concentration, or drying under nitrogen.

The present invention further provide another method for preparing the above-mentioned pharmaceutically acceptable compound, including the following steps: mixing the basic group-containing compound of the formula (I) in a free base form or in a salt form and the carboxyl group-containing agent in a base form or in a salt form to form a mixture; and pulverizing the mixture by a physical-mechanical means to form the pharmaceutically acceptable compound. Herein, an example of the physical-mechanical means is pulverizing the mixture in a motar with a pestle.

Additionally, the obtained pharmaceutically acceptable salt can be further purified by dissolving the salt in a suitable solvent, concentrated and recrystallized by evaporating the solvent by natural evaporation, vacuum concentration, or drying under nitrogen.

The present invention also provides a pharmaceutical formulation which comprises the above-mentioned pharmaceutically acceptable compound and a pharmaceutically acceptable carrier. The pharmaceutical formulation is suitable for use in transnasal, transdermal, rectal, oral treatment or parenteral injection.

These pharmaceutically acceptable salts may be used to manufacture medicaments for treating and/or preventing hyperglycemic disease and treatment and/or prophylaxis of cardiac diseases, including cardiac arrhythmia, myocardial ischemia or myocardial infarction, and sudden death caused by cardiac arrhythmia or acute myocardial infarction, or to manufacture medicaments for preventing or treating ischemic diseases, and the ischemic diseases may include ischemic cerebral apoplexy, ischemic cerebral thrombosis, ischemic cerebral embolism, hypoxic ischemic encephlopathy, ischemic cardiac disease or ischemic enteropathy etc.

Also within the scope of this invention is a method for treating oxidative stress induced diseases by administering to a subject in need thereof an effective amount of the above-mentioned pharmaceutically acceptable compound.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
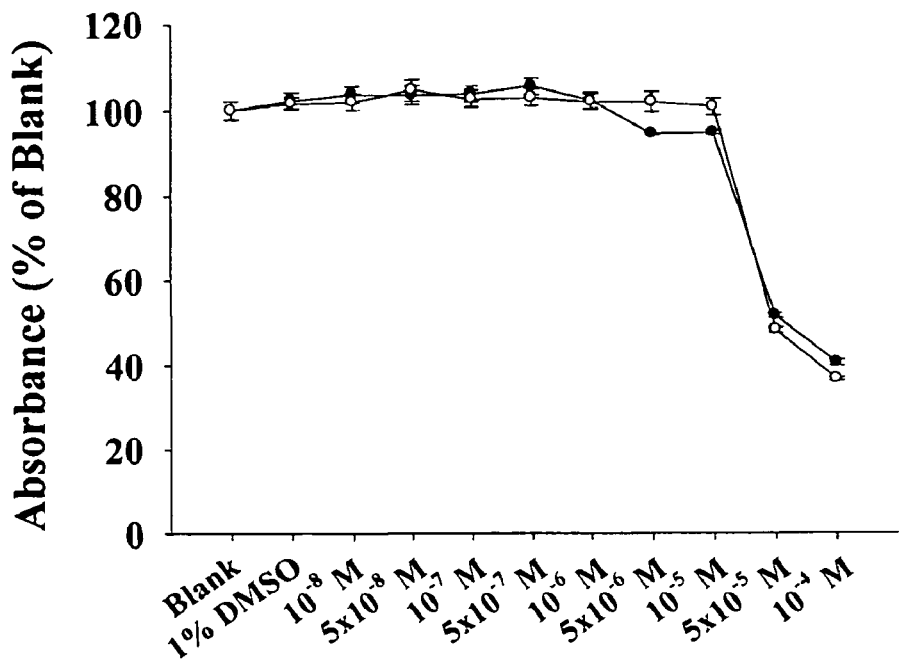
FIG. 1 shows a diagram of absorbance of DPPH versus the concentration of Compounds 1 and 2 (-■- for Compound 1, -○- for Compound 2).

According to the present invention, the pharmaceutically acceptable salts may be formed by (1) the interaction of the acid (i.e. the carboxyl group-containing agent) with the base (i.e. the aporphine compound); and (2) the solvent dissolution-removal or pulverization method employed in the present invention which further enhances the salt forming process. The pharmaceutically acceptable salts may be readily filtered and easily dried, and, if necessary, can be easily re-purified by re-dissolving the salt in a suitable solvent followed by drying to remove the solvent, or followed by mixing the resulting solution with another suitable solvent to precipitate the pharmaceutically acceptable compound.

For example, the pharmaceutically acceptable salts may be prepared in accordance with the following procedure.

To a round bottom flask equipped with a magnetic stirrer was charged with an aporphine compound, a chosen carboxyl group-containing agent, and an appropriate solvent system. The resulting reaction mixture was allowed to agitate at a certain temperature for a certain period of time until it was dissolved completely. The resulting solution was concentrated via reduced pressure distillation, or the resulting solution was mixed with another suitable solvent, and the desired aporphine compound-carboxylic acid salt was thus obtained.

In addition, with regard to aporphine compounds included in pharmaceutically acceptable salts, some aporphine derivatives (e.g. thaliporphine, norglaucine, N-[2-(2-methoxyphenoxy)ethyl]norglaucine) are known, while some aporphine derivatives are novel and cannot be commercially provided (such as theses above-mentioned exemplary compounds 1-7). Thereby the present invention provides methods for preparing novel aporphine derivatives.

Northaliporphine can be found within the U.S. Pat. No.4,202,980, norglaucine can be found within the U.S. Pat. No.4,120,964, boldine, thaliporphine, glaucine, laurolitsine, can be employed as the starting material to generate the aporphine derivatives of the general formula (I). The boldine is available from the market, the thaliporphine and the glaucine can be synthesized according to U.S. Pat. No.6,313,134 B1, and the norglaucine, the northaliporphine and the laurolitsine can be synthesized according to U.S. Pat. No. 7,294,715 B2.

An acylation or alkylation reaction may be involved in the preparation of the aporphine derivatives. These various aporphine derivatives can be achieved by various approaches (eg. Acylation by acyl halide, acyl anhydride, or mixed anhydride; alkylation from a suitable alkylating agent, reductive amination from a suitable aldehyde and hydrogenation from a suitable imine, etc.). By using the above preparation processes, the general formula (I) can be synthesized.

Accordingly, theses above-mentioned exemplary compounds 1-7 can be obtained by the following synthesis schemes 1-7, respectively.

The following examples are illustrative, but not limiting the scope of the present invention. Reasonable variations, such as those occur to reasonable artisan, can be made herein without departing from the scope of the present invention.

PREPARATION EXAMPLE 1

Preparation of Compound 1

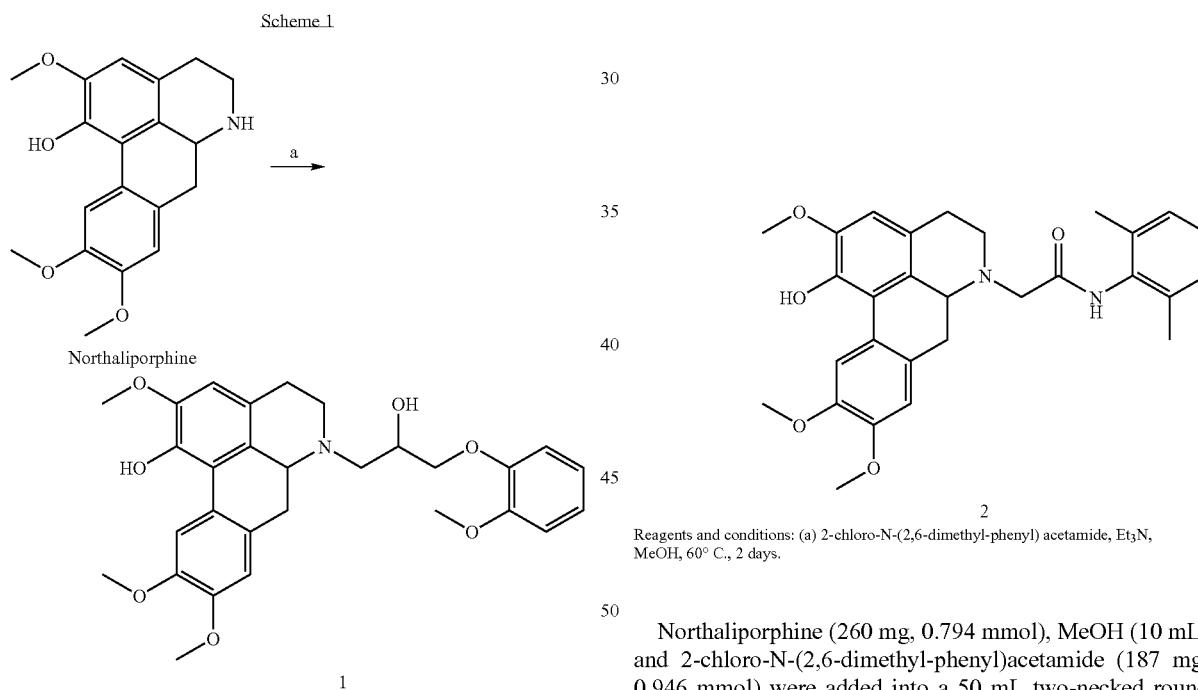

Reagents and conditions: (a) 2-[(2-methoxy-phenox)methyl] oxirane, MeOH, 70° C., 16 hrs.

Northaliporphine (380 mg, 1.16 mmol), methanol (MeOH, 10 mL) and 2-[(2-methoxy-phenox)methyl]oxirane (167 mg, 0.92 mmol) were added into a 50 mL round bottom flask and stirred at 70° C. for 16 hours. The mixture was evaporated to dryness. The residue was purified by chromatography (silica gel: 70-230 mesh 30 g, mobile phase: 2% MeOH/$CH_2Cl_2$, v/v) to obtain Compound 1, $R_f$ 0.15 (2% MeOH/$CH_2Cl_2$, v/v); Physical data were as follows: mp: 63-68° C. ($CH_2Cl_2$); IR(KBr) $v_{max}$: 3500, 2931, 1605, 1506, 1464, 1253, 1112 $cm^{-1}$; $^1$H NMR ($CDCl_3$, 500 MHz): δ 8.00 (s, 1H), 6.98-6.88 (m, 4H), 6.75 and 6.73 (s, 1H), 6.53 (s, 1H), 6.12 (brs, 1H), 4.24-4.07 (m, 3H), 3.90 (s, 3H), 3.88 (s, 3H), 3.85 (s, 3H), 3.79 (s, 3H), 3.39-2.53 (m, 9H); EIMS (70 eV): m/z (%) 507 $[M]^+$, 339 (100).

PREPARATION EXAMPLE 2

Preparation of Compound 2

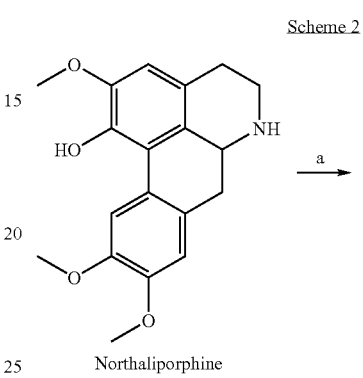

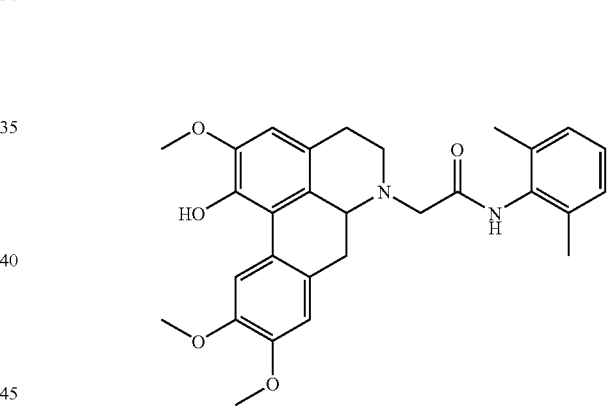

Reagents and conditions: (a) 2-chloro-N-(2,6-dimethyl-phenyl) acetamide, $Et_3N$, MeOH, 60° C., 2 days.

Northaliporphine (260 mg, 0.794 mmol), MeOH (10 mL) and 2-chloro-N-(2,6-dimethyl-phenyl)acetamide (187 mg, 0.946 mmol) were added into a 50 mL two-necked round bottom flask. Then triethylamine ($Et_3N$, 0.5 mL, 3.55 mmol) was dropped into the mixture, and the reaction was allowed to proceed at 60° C. for two days. The mixture was evaporated to dryness. The residue was partitioned with water (50 mL) and dichloromethane (50 mL×3), and the organic layers were collected. The organic layer was dried with anhydrous $MgSO_4$ and then filtered. The filtrate was evaporated to dryness. The residue was purified by chromatography (silica gel: 70-230 mesh 30 g, mobile phase: 2% MeOH/$CH_2Cl_2$, v/v) to obtain Compound 2, $R_f$ 0.58 (2% MeOH/$CH_2Cl_2$, v/v); Physical data were as follows: mp: 205-207° C. ($CH_2Cl_2$); IR(KBr) $v_{max}$: 3312, 2945, 1663,1 604, 1511, 1477, 1258, 1087 $cm^{-1}$; $^1$H NMR($CDCl_3$, 500 MHz): δ 8.99 (s, 1H), 8.02 (s, 1H), 7.10 (s, 3H), 6.76 (s, 1H), 6.56 (s, 1H), 6.12 (s, 1H), 3.91 (s, 9H), 3.77-3.11 (m, 5H), 2.98-2.86 (m, 2H), 2.75-2.69 (m, 2H), 2.25 (s, 6H); EIMS (70 eV): m/z (%) 488 [M]+, 326 (100).

PREPARATION EXAMPLE 3

Preparation of Compound 3

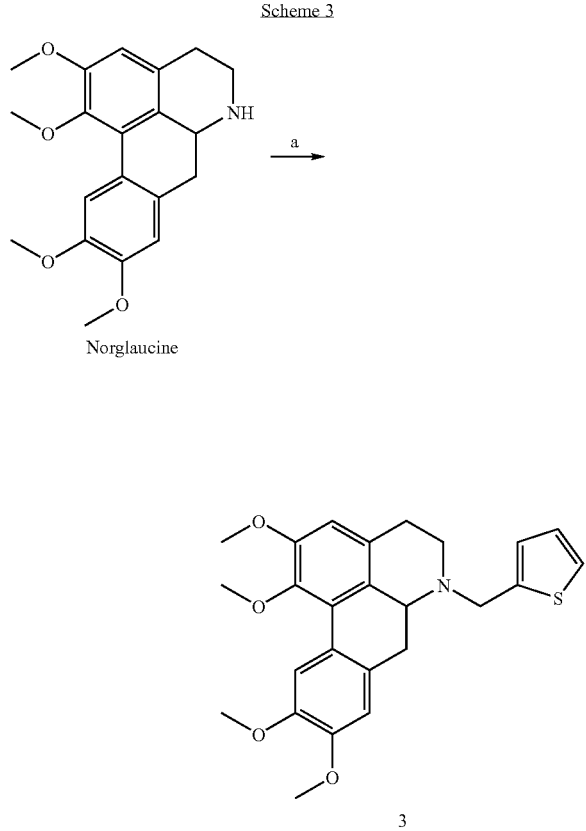

3

Reagents and conditions: (a) 2-thiophenecarboxaldehyde, MgSO₄, MeOH, AcOH, NaBH₃CN, 70° C., 4 hrs.

Norglaucine (300 mg, 0.88 mmol), MgSO₄ (1 g), MeOH (7 mL), 2-thiophenecarboxaldehyde (0.14 mL, 1.5 mmol) and AcOH (0.5 mL, 8.88 mmol) were added into a 100 mL two-necked round bottom flask and stirred at room temperature. Sodium cyanoborohydride (NaBH₃CN, 100 mg, 1.58 mmol) was added into the mixture after 1 hour, and the reaction was allowed to proceed at 70° C. for 4 hours. The mixture was evaporated to dryness. The residue was partitioned with water (50 mL) and dichloromethane (50 mL×2), and the organic layers were collected. The organic layer was dried with anhydrous MgSO₄ and then filtered. The filtrate was evaporated to dryness. The residue was purified by chromatography (silica gel: 230-400 mesh 30 g, mobile phase: EA/Hex=1/2, v/v) to obtain Compound 3, $R_f$ 0.77 (EA/Hex=1/1, v/v); Physical data were as follows: mp: 143-148° C. (CH₂Cl₂); IR(KBr) $v_{max}$: 2958, 1578, 1514, 1466, 1110 cm⁻¹; ¹H NMR(CDCl₃, 400 MHz):δ 8.05 (s, 1H), 7.22-7.20 (m, 1H), 6.96-6.95 (m, 2H), 6.77 (s, 1H), 6.57 (s, 1H), 4.35 (d, J=14.6 Hz, 1H), 3.92 (s, 3H), 3.88 (s, 3H), 3.86 (s, 3H), 3.85 (d, J=14.6 Hz, 1H), 3.62 (s, 3H), 3.36-3.33 (m, 1H), 3.15-3.09 (m, 2H), 3.05-3.02 (m, 1H), 2.71-2.60 (m, 2H), 2.51-2.44 (m, 1H); EIMS (70 eV): m/z (%) 437 [M]+, 97 (100).

PREPARATION EXAMPLE 4

Preparation of Compound 4

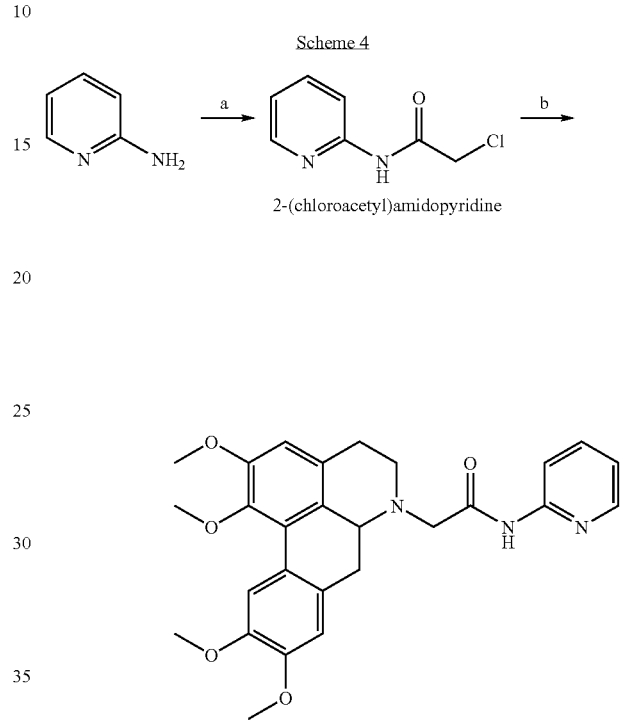

4

Reagents and conditions: (a) chloroacetyl chloride, Et₃N, CH₂Cl₂, rt, 17 hrs; (b) Norglaucine, K₂CO₃, CH₃CN, 80° C., 16 hrs.

2-Aminopyridine (2 g, 21.3 mmol), chloroacetyl chloride (2.5 mL, 31.4 mmol) and Et₃N (4.4 mL, 31.8 mmol) were dissolved in dichloromethane (CH₂Cl₂, 100 mL). The reaction mixture was stirred at room temperature for 17 hours, after which the organic phase was washed with an aqueous solution of NaHCO₃ (10%, w/v). The organic layer was dried with anhydrous MgSO₄ and then filtered. The filtrate was evaporated to dryness. The residue was purified using flash chromatography (CH₂Cl₂), yielding 2.46 g (68%) of 2-(chloroacetyl)amidopyridine.

Norglaucine (0.3 g, 0.88 mmol), 2-(chloroacetyl)amidopyridine (0.15 g, 0.88 mmol) and potassium carbonate (K₂CO₃, 0.3 g, 1.8 mmol) in acetonitrile (CH₃CN, 7 mL) was stirred at 80° C. for 16 hours. The mixture was evaporated to dryness. The residue was partitioned with water (50 mL) and dichloromethane (50 mL×2). The organic layer was dried with anhydrous MgSO₄ and then filtered. The filtrate was evaporated to dryness. The residue was purified by chromatography (silica gel: 230-400 mesh 30 g, mobile phase: EA/Hex=1:1, v/v) to obtain Compound 4, $R_f$ 0.75 (100% EA); Physical data were as follows: mp: 43-46° C. (CH₂Cl₂); IR(KBr) $v_{max}$: 3300, 2933, 1693, 1578, 1513, 1434, 1257, 1091 cm⁻¹; ¹H NMR (CDCl₃, 400 MHz):δ 9.87 (s, 1H), 8.29-8.24 (m, 2H), 8.04 (s, 1H), 7.73-7.69 (m, 1H), 7.04-7.01 (m, 1H), 6.70 (s, 1H), 6.61 (s, 1H), 3.89 (s, 3H), 3.87 (s, 6H), 3.63 (s, 3H), 3.61

(d, J=17.2 Hz, 1H), 3.46-3.42 (m, 1H), 3.30-3.23 (m, 2H), 3.13-3.08 (m, 1H), 2.92-2.68 (m, 4H); ESI-MS (30 V): m/z (%) 476 [M+H]$^+$ (100).

PREPARATION EXAMPLE 5

Preparation of Compound 5

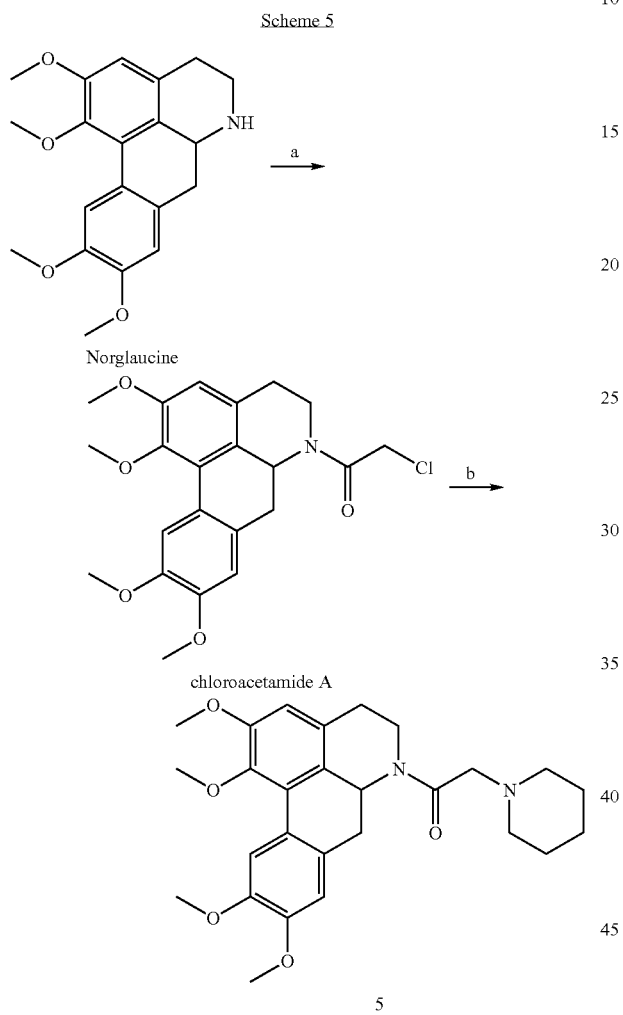

Reagents and conditions: (a) chloroacetyl chloride, Et$_3$N, CH$_2$Cl$_2$, rt, 1 hr; (b) piperidine, CH$_3$CN, 80° C., 16 hrs.

Norglaucine (500 mg, 1.47 mmol), chloroacetyl chloride (0.35 mL, 4.4 mmol) and CH$_2$Cl$_2$ (7 mL) were added into a 100 mL round bottom flask. Then 0.6 mL of Et$_3$N was dropped into a round bottom flask at room temperature for 1 hour. The reaction solution was poured into 50 mL water, and the mixture was stirred and adjusted with ammonia water to pH 8.0. The mixture was extracted two times with dichloromethane, and the organic layers were collected. The organic layer was dried with anhydrous MgSO$_4$ and then filtered. The filtrate was evaporated to dryness. The residue was purified by chromatography (silica gel: 230-400 mesh 30 g, mobile phase: EA/Hex=1/1, v/v) to obtain chloroacetamide A, R$_f$ 0.46 (EA/Hex=1/1, v/v).

Chloroacetamide A (300 mg, 0.719 mmol) and piperidine (0.5 mL) in CH$_3$CN (7 mL) was stirred at 80° C. for 16 hours and the reaction progress was monitored by silica TLC. The mixture was evaporated to dryness. The residue was partitioned with water (50 mL) and dichloromethane (50 mL×2), and the organic layers were collected. The organic layer was dried with anhydrous MgSO$_4$ and then filtered. The filtrate was evaporated to dryness. The residue was purified by chromatography (silica gel: 230-400 mesh 20 g, mobile phase: EA/Hex=1:1, v/v) to obtain Compound 5, R$_f$ 0.33 (100% EA); Physical data were as follows: mp: 108-110° C. (CH$_2$Cl$_2$); IR(KBr) ν$_{max}$: 2934, 1640, 1514, 1451, 1254, 1102 cm$^{-1}$; $^1$H NMR(CDCl$_3$,400MHz):δ 8.12 (s, 1H), 6.76 (s, 1H), 6.62 (s, 1H), 5.00-4.00 (m, 2H), 3.89 (s, 3H), 3.88 (s, 6H), 3.65 (s, 3H), 3.33-2.66 (m, 7H), 2.43 (m, 4H), 1.57-1.56 (m, 4H), 1.42 (m, 2H); EIMS (70 eV): m/z (%) 466 [M]$^+$, 381 (100).

PREPARATION EXAMPLE 6

Preparation of Compound 6

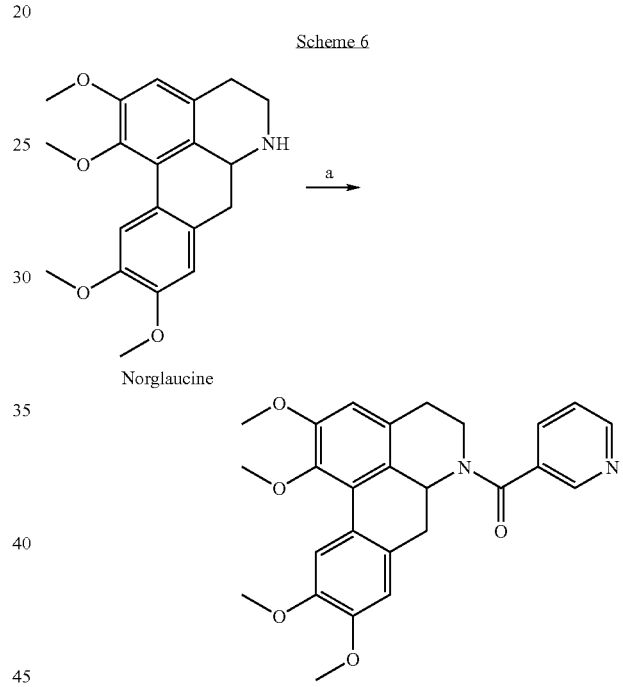

Reagents and conditions: (a) nicotinoyl chloride, Et$_3$N, CH$_3$CN, rt, 1 hr.

Nicotinic acid (0.1 g, 0.86 mmol) was heated under reflux with thionyl chloride (1.0 mL, 12.4 mmol) for 1 hour. The solvent was evaporated under reduced pressure. An off-white solid was formed and the product was used immediately for the next step.

Norglaucine (0.2 g, 0.58 mmol) and Et$_3$N (0.23 mL, 1.56 mmol) were dissolved in CH$_3$CN (1 mL). The mixture was reacted with nicotinoyl chloride in CH$_3$CN (1 mL) by adding it drop by drop at room temperature. The mixture was stirred at room temperature for 1 hour, and the solvent was evaporated under reduced pressure. The residue was partitioned with water (10 mL) and dichloromethane (10 mL), and the organic layer was evaporated under reduced pressure. The residue was purified by chromatography (silica gel: 230-400 mesh 15 g, mobile phase: EA/Hex=1:1, v/v) to obtain Compound 6, R$_f$ 0.3 (100% EA); Physical data were as follows: mp: 178-181° C. (CH$_2$Cl$_2$); IR(KBr) ν$_{max}$: 2947, 1632, 1514, 1466, 1265, 1099 cm$^{-1}$; $^1$H NMR (CDCl$_3$, 400 MHz):δ 8.70

(s, 1H), 8.67 (brd, J=4.1 Hz, 1H), 8.14 (s, 1H), 7.78 (brd, J=7.7 Hz, 1H), 7.39-7.36 (m, 1H), 6.78 (s, 1H), 6.62 (s, 1H), 3.90 (s, 6H), 3.88 (s, 3H), 3.66 (s, 3H), 3.72-2.64 (m, 6H); EIMS (70 eV): m/z (%) 446 [M]$^+$ (100).

PREPARATION EXAMPLE 7

Preparation of Compound 7

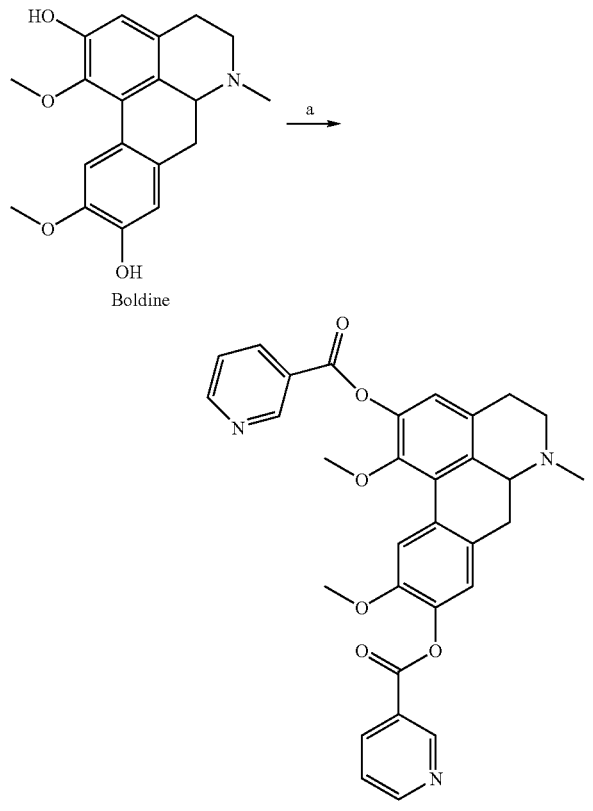

Scheme 7

Boldine

7

Reagents and conditions: (a) nicotinoyl chloride, Et$_3$N, toluene, 80° C., 17 hrs.

Nicotinic acid (865 mg, 7 mmol) was heated under reflux with thionyl chloride (3.5 mL, 48.5 mmol) for 1 hour. The solvent was evaporated under reduced pressure. An off-white solid was formed and the product was used immediately for the next step.

Boldine (1 g, 3.1 mmol), nicotinoyl chloride (1 g, 7.1 mmol), Et$_3$N (1.3 mL, 9.3 mmol) and toluene (12 mL) were added into a 100 mL round bottom flask. The mixture was stirred at 80° C. for 17 hours and the reaction progress was monitored by silica TLC. After removing the salt by filtration, the filtrate was evaporated to dryness. The residue was partitioned with water (75 mL) and dichloromethane (75 mL×3), and the organic layers were collected. The organic layer was dried with anhydrous MgSO$_4$ and then filtered. The filtrate was evaporated to dryness. The residue was purified by chromatography (silica gel: 230-400 mesh 50 g, mobile phase: MeOH/CH$_2$Cl$_2$=1/8, v/v) to obtain Compound 7, R$_f$ 0.58 (MeOH/CH$_2$Cl$_2$=1/6, v/v); Physical data were as follows: mp: 110-113° C. (MeOH); IR(KBr) v$_{max}$: 2955, 1744, 1589, 1421, 1273, 1096 cm$^{-1}$; $^1$H NMR (CD$_3$OD, 400 MHz):δ 9.25 (d, J=2.0 Hz, 1H), 9.19 (d, J=2.0 Hz, 1H), 8.77 (dd, J=5.1, 1.4 Hz, 1H), 8.74 (dd, J=5.0, 1.4 Hz, 1H), 8.53-8.50 (m, 1H), 8.47-8.45 (m, 1H), 8.05 (s, 1H), 7.60-7.54 (m, 1H), 7.14 (s, 1H), 6.99 (s, 1H), 3.73 (s, 3H), 3.52 (s, 3H), 2.50 (s, 3H), 3.15-2.46 (m, 7H); ESI-MS (30 V): m/z (%) 538 [M+H]$^+$, 106 (100).

In the following examples, a prepared salt of an aporphine derivative and a carboxyl group-containing agent are characterized by their distinctive physical and chemical properties, which are different from either the carboxyl group-containing agent alone or the aporphine derivative alone, as demonstrated by the FTIR, MS, and NMR analyses.

Infrared spectroscopy (IR) has long been used in the evaluation of chemical compounds. Fourier Transform Infrared Spectroscopy (FT-IR) has been used to identify and evaluate organic and inorganic materials or compounds. Using FTIR, spectral data is collected and converted from an interference pattern to a spectrum. The system provides for subtractive elimination of background spectra, such that particular chemical compounds can be identified by a molecular "fingerprint".

Electro-spray Ionization Mass Spectroscopy (ESI-MS) can be used to determine the molecular weights and the chemical structures of the pharmaceutically acceptable salts.

Nuclear magnetic resonance solutions provide useful data regarding the type, quantity and arrangement of different atoms in chemical systems, liquids and solids.

EXAMPLE 1

Preparation of an Atorvastatin salt of the Thaliporphine by Thaliporphine Free Base and Atorvastatin Free Acid Thaliporphine free base (0.0741 g, 0.217 mmol) and Atorvastatin free acid (0.1262 g, 0.226 mmol) were thoroughly mixed and then added to 5 mL of methanol. The resultant mixture was then stirred until the mixture was dissolved. The Atorvastatin salt of Thaliporphine was obtained as removing the methanol by reduced-pressure or vacuum concentration, or drying under nitrogen until the sample was completely dried.

[Thaliporphine]
  IR(KBr) v$_{max}$: 3272, 1602, 1517, 1465, 1255, 1112, 1083 cm$^{-1}$
  Molecular Weight: 341
[Atorvastatin]
  IR(KBr) v$_{max}$: 3380, 1717, 1640, 1508 cm$^{-1}$
  Molecular Weight: 558
[Atorvastatin Salt of Thaliporphine]
  IR(KBr) v$_{max}$: 3402, 2959, 1663, 1596, 1510, 1465, 1253, 1107 cm$^{-1}$
  Molecular Weight: 899
  ESI-MS (30V): m/z (%) 900 [M+H]$^+$, 342 (100)
  $^1$H NMR (CD$_3$OD, 500 MHz):δ 8.14 (s, 1H), 7.29-7.28 (m, 2H), 7.23-7.19 (m, 4H), 7.13-7.00 (m, 8H), 6.89 (s, 1H), 6.67 (s, 1H), 4.06-3.90 (m, 2H), 3.88 (s, 3H), 3.85 (s, 3H), 3.83 (s, 3H), 3.66-3.58 (m, 2H), 3.39-3.35 (m, 2H), 3.19-3.16 (m, 2H), 2.99-2.93 (m, 1H), 2.82-2.78 (m, 5H), 2.65 (t, J=14.0 Hz, 1H), 2.35-2.24 (m, 2H), 1.71-1.65 (m, 2H), 1.53-1.48 (m, 2H), 1.46 (d, J=7.0 Hz, 6H).

EXAMPLE 2

Preparation of a Telmisartan salt of the Thaliporphine by Thaliporphine Free Base and Telmisartan Free Acid Thaliporphine free base (0.12 g, 0.351 mmol) and Telmisartan free acid (0.18 g, 0.351 mmol) were thoroughly mixed and then added to 5 mL of methanol. The resultant mixture was then stirred until the mixture was dissolved. The Telmisartan salt of Thaliporphine was obtained as removing the methanol by reduced-pressure or vacuum concentration, or drying under nitrogen until the sample was completely dried.
[Thaliporphine]
 IR(KBr) $v_{max}$: 3272, 1602, 1517, 1465, 1255, 1112, 1083 cm$^{-1}$
 Molecular Weight: 341
[Telmisartan]
 IR(KBr) $v_{max}$: 3431, 3059, 2963, 1696, 1461, 1267, 742 cm$^{-1}$
 Molecular Weight: 514
[Telmisartan Salt of Thaliporphine]
 IR(KBr) $v_{max}$: 3392, 2957, 1601, 1516, 1461, 1253, 1106 cm$^{-1}$
 Molecular Weight: 855
 ESI-MS (30V): m/z (%) 856 [M+H]$^+$, 279 (100)
 $^1$H NMR (CD$_3$OD, 500 MHz):δ 8.12 (s, 1H), 7.63 (d, J=6.5 Hz, 2H), 7.47-7.46 (m, 2H), 7.40 (t, J=7.5 Hz, 2H), 7.29-7.22 (m, 6H), 7.03 (d, J=7.0 Hz, 2H), 6.82 (s, 1H), 6.60 (s, 1H), 5.45-5.37 (m, 2H), 3.84 (s, 3H), 3.81 (s, 9H), 3.69 (s, 3H), 3.60-3.58 (m, 2H), 3.17-2.95 (m, 5H), 2.67 (s, 3H), 2.51-2.45 (m, 2H), 1.82-1.81 (m, 2H), 1.02 (t, J=7.5 Hz, 3H).

EXAMPLE 3

Preparation of a Captopril Salt of the Thaliporphine by Thaliporphine Free Base and Captopril Free Acid Thaliporphine free base (0.1222 g, 0.356 mmol) and Captopril free acid (0.078 g, 0.359 mmol) were thoroughly mixed and then added to 2 mL of methanol. The resultant mixture was then stirred until the mixture was dissolved. The Captopril salt of Thaliporphine was obtained as removing the methanol by reduced-pressure or vacuum concentration, or drying under nitrogen until the sample was completely dried.
[Thaliporphine]
 IR(KBr) $v_{max}$: 3272, 1602, 1517, 1465, 1255, 1112, 1083 cm$^{-1}$
 Molecular Weight: 341
[Captopril]
 IR(KBr) $v_{max}$: 2980, 2566, 1748, 1589 cm$^{-1}$
 Molecular Weight: 217
[Captopril Salt of Thaliporphine]
 IR(KBr) $v_{max}$: 3421, 2966, 1607, 1517, 1464, 1396, 1255, 1106 cm$^{-1}$
 Molecular Weight: 558
 ESI-MS (30V): m/z (%) 559 [M+H]$^+$, 342 (100)
 $^1$H NMR (CD$_3$OD, 500 MHz):δ 8.14 (s, 1H), 6.90 (s, 1H), 6.70 (s, 1H), 4.39-4.36 (m, 1H), 3.89 (s, 3H), 3.86 (s, 3H), 3.83 (s, 3H), 3.69-3.53 (m, 4H), 3.28-3.15 (m, 3H), 2.94 (s, 3H), 2.86-2.66 (m, 4H), 2.44-2.33 (m, 1H), 2.21-2.11 (m, 2H), 2.01-1.91 (m, 2H), 1.13 (d, J=7 Hz, 3H).

EXAMPLE 4

Preparation of a Bezafibrate Salt of the N-[2-(2-methoxyphenoxy)ethyl]norglaucine by N-[2-(2-methoxyphenoxy) ethyl]norglaucine Free Base and Bezafibrate Free Acid N-[2-(2-methoxyphenoxy)ethyl]norglaucine free base (0.128 g, 0.26 mmol) and Bezafibrate free acid (0.094 g, 0.26 mmol) were thoroughly mixed and then added to 5 mL of methanol. The resultant mixture was then stirred until the mixture was dissolved. The Bezafibrate salt of N-[2-(2-methoxyphenoxy)ethyl]norglaucine was obtained as removing the methanol by reduced-pressure or vacuum concentration, or drying under nitrogen until the sample was completely dried.
[N-[2-(2-methoxyphenoxy)ethyl]norglaucine]
 IR(KBr) $v_{max}$: 2933, 1593, 1506, 1463, 1253, 1113, 1095, 1025 cm$^{-1}$
 Molecular Weight: 491
[Bezafibrate]
 IR(KBr) $v_{max}$: 3358, 2886, 1718, 1610, 1549, 1147 cm$^{-1}$
 Molecular Weight: 361
[Bezafibrate salt of N-[2-(2-methoxyphenoxy)ethyl]norglaucine]
 IR(KBr) $v_{max}$: 3402, 2935, 1595, 1508, 1465, 1253, 1110 cm$^{-1}$
 Molecular Weight: 852
 ESI-MS (30V): m/z (%) 853 [M+H]$^+$, 492 (100)
 $^1$H NMR (CD$_3$OD, 500 MHz):δ 8.00 (s, 1H), 7.72 (d, J=7.5 Hz, 2H), 7.43 (d, J=7.5 Hz, 2H), 7.07 (d, J=8.0 Hz, 2H), 7.01 (d, J=8.0 Hz, 1H), 6.95-6.90 (m, 4H), 6.82 (d, J=8.0 Hz, 2H), 6.77 (s, 1H), 4.37-4.33 (m, 2H), 3.86 (s, 6H), 3.85 (s, 3H), 3.70 (s, 3H), 3.64 (s, 3H), 3.51 (t, J=7.0 Hz, 2H), 3.49-2.87 (m, 8H), 2.81 (t, J=7.0 Hz, 2H), 1.50 (s, 6H).

EXAMPLE 5

Preparation of a Repaglinide Salt of the Glaucine by Glaucine Free Base and Repaglinide Free Acid Glaucine free base (0.2 g, 0.563 mmol) and Repaglinide free acid (0.255 g, 0.563 mmol) were thoroughly mixed and then added to 5 mL of methanol. The resultant mixture was then stirred until the mixture was dissolved. The Repaglinide salt of Glaucine was obtained as removing the methanol by reduced-pressure or vacuum concentration, or drying under nitrogen until the sample was completely dried.
[Glaucine]
 IR(KBr) $v_{max}$: 2962, 1597, 1516, 1463, 1251, 1113, 1091 cm$^{-1}$
 Molecular Weight: 355
[Repaglinide]
 IR(KBr) $v_{max}$: 3308, 2935, 1687, 1637, 1217 cm$^{-1}$
 Molecular Weight: 452
[Repaglinide Salt of Glaucine]
 IR(KBr) $v_{max}$: 3292, 2934, 1653, 1609, 1516, 1464, 1110 cm$^{-1}$
 Molecular Weight: 807
 ESI-MS (30V): m/z (%) 808 [M+H]$^+$, 162 (100)
 $^1$H NMR (CD$_3$OD, 500 MHz):δ 7.92 (s, 1H), 7.46 (d, J=7.7 Hz, 1H), 7.17 (brd, J=7.3 Hz, 1H), 7.10-7.03 (m, 2H), 6.97-6.93 (m, 1H), 6.85 (s, 2H), 6.79 (brd, J=7.3 Hz, 1H), 6.68 (s, 1H), 5.53-5.50 (m, 1H), 3.93 (q, J=6.9 Hz, 2H), 3.79 (s, 3H), 3.78 (s, 3H), 3.77 (s, 3H), 3.56 (s, 3H), 3.45 (s, 2H), 3.45-3.39 (m, 2H), 3.12-3.08 (m, 2H), 2.97 (brm, 2H), 2.85-2.71 (m, 3H), 2.69 (s, 3H), 2.57 (t, J=13.8 Hz, 2H), 1.67 (brm, 2H), 1.56-1.36 (m, 7H), 1.27 (t, J=6.9 Hz, 3H), 0.87 (d, J=6.1 Hz, 3H), 0.85 (d, J=6.1 Hz, 3H).

EXAMPLE 6

Preparation of a Acetylcysteine Salt of the Thaliporphine Derivative by Thaliporphine Free Base and Acetylcysteine Free Acid Thaliporphine free base (0.1353 g, 0.396 mmol) and Acetylcysteine free acid (0.0647 g, 0.396 mmol) were thoroughly mixed and then added to 5 mL of methanol. The resultant mixture was then stirred until the mixture was dissolved. The Acetylcysteine salt of Thaliporphine was obtained as removing the methanol by reduced-pressure or vacuum concentration, or drying under nitrogen until the sample was completely dried.

[Thaliporphine]
IR(KBr) $v_{max}$: 3272, 1602, 1517, 1465, 1255, 1112, 1083 cm$^{-1}$
Molecular Weight: 341

[Acetylcysteine]
IR(KBr) $v_{max}$: 3374, 2547, 1718, 1534 cm$^{-1}$
Molecular Weight: 163

[Acetylcysteine Salt of Thaliporphine]
IR(KBr) $v_{max}$: 3381, 2938, 2558, 1605, 1480, 1254, 1105 cm$^{-1}$
Molecular Weight: 504
ESI-MS (30V): m/z (%) 505 [M+H]$^+$, 342 (100)
$^1$H NMR (CD$_3$OD, 500 MHz):δ 8.14 (s, 1H), 6.91 (s, 1H), 6.71 (s, 1H), 4.43 (brs, 1H), 4.00-3.98 (m, 1H), 3.89 (s, 3H), 3.85 (s, 3H), 3.83 (s, 3H), 3.50-3.48 (m, 3H), 3.18-3.15 (m, 2H), 2.91 (brs, 3H), 2.85-2.82 (m, 1H), 2.79-2.76 (m, 2H), 1.99 (s, 3H).

EXAMPLE 7

Preparation of a Chromocarb Salt of the Thaliporphine by Thaliporphine Free Base and Chromocarb Free Acid Thaliporphine free base (0.1285 g, 0.376 mmol) and Chromocarb free acid (0.0715 g, 0.376 mmol) were thoroughly mixed and then added to 2 mL of methanol. The resultant mixture was then stirred until the mixture was dissolved. The Chromocarb salt of Thaliporphine was obtained as removing the methanol by reduced-pressure or vacuum concentration, or drying under nitrogen until the sample was completely dried.

[Thaliporphine]
IR(KBr) $v_{max}$: 3272, 1602, 1517, 1465, 1255, 1112, 1083 cm$^{-1}$
Molecular Weight: 341

[Chromocarb]
IR(KBr) $v_{max}$: 3080, 1737, 1631, 1239 cm$^{-1}$
Molecular Weight: 190

[Chromocarb Salt of Thaliporphine]
IR(KBr) $v_{max}$: 3402, 1632, 1613, 1518, 1465, 1254, 1105 cm$^{-1}$
Molecular Weight: 531
ESI-MS (30V): m/z (%) 532 [M+H]$^+$, 342 (100)
$^1$H NMR (CD$_3$OD, 500 MHz):δ 8.09 (s, 1H), 8.07-8.05 (m, 1H), 7.77-7.73 (m, 1H), 7.62-7.61 (m, 1H), 7.44-7.42 (m, 1H), 6.90 (s, 1H), 6.89 (s, 1H), 6.68 (s, 1H), 4.19-4.17 (m, 1H), 3.87 (s, 3H), 3.84 (s, 3H), 3.82 (s, 3H), 3.76-3.26 (m, 4H), 3.12 (s, 3H), 2.98-2.81 (m, 2H).

EXAMPLE 8

Preparation of a Atorvastatin Salt of the Compound 1 by Compound 1 Free Base and Atorvastatin Free Acid Compound 1 free base (0.05 g, 0.099 mmol) and Atorvastatin free acid (0.055 g, 0.099 mmol) were thoroughly mixed and then added to 5 mL of methanol. The resultant mixture was then stirred until the mixture was dissolved. The Atorvastatin salt of Compound 1 was obtained as removing the methanol by reduced-pressure or vacuum concentration, or drying under nitrogen until the sample was completely dried.

[Compound 1]
IR(KBr) $v_{max}$: 3500, 2931, 1605, 1506, 1464, 1253, 1112 cm$^{-1}$
Molecular Weight: 507

[Atorvastatin]
IR(KBr) $v_{max}$: 3380, 1717, 1640, 1508 cm$^{-1}$
Molecular Weight: 558

[Atorvastatin Salt of Compound 1]
IR(KBr) $v_{max}$: 3402, 2936, 1655, 1595, 1508, 1438, 1254, 1106 cm$^{-1}$
Molecular Weight: 1065
ESI-MS (30V): m/z (%) 1066 [M+H]$^+$, 279 (100)
$^1$H NMR (CD$_3$OD, 400 MHz):δ 8.04 and 8.03 (s, 1H), 7.21-7.10 (m, 4H), 7.05-6.88 (m, 14H), 6.75 and 6.73 (s, 1H), 6.59 and 6.57 (s, 1H), 4.24-4.22 (m, 1H), 4.00-3.72 (m, 7H), 3.80 (s, 3H), 3.74 (s, 9H), 3.29-2.50 (m, 8H), 2.24-2.20 (m, 2H), 1.62-1.42 (m, 4H), 1.38 (d, J=7.1 Hz, 6H).

EXAMPLE 9

Preparation of a Bezafibrate Salt of the Compound 1 by Compound 1 Free Base and Bezafibrate Free Acid Compound 1 free base (0.04 g, 0.079 mmol) and Bezafibrate free acid (0.028 g, 0.079 mmol) were thoroughly mixed and then added to 5 mL of methanol. The resultant mixture was then stirred until the mixture was dissolved. The Bezafibrate salt of Compound 1 was obtained as removing the methanol by reduced-pressure or vacuum concentration, or drying under nitrogen until the sample was completely dried.

[Compound 1]
IR(KBr) $v_{max}$: 3500, 2931, 1605, 1506, 1464, 1253, 1112 cm$^{-1}$
Molecular Weight: 507

[Bezafibrate]
IR(KBr) $v_{max}$: 3358, 2886, 1718, 1610, 1549, 1147 cm$^{-1}$
Molecular Weight: 361

[Bezafibrate Salt of Compound 1]
IR(KBr) $v_{max}$: 3418, 2938, 1640, 1596, 1508, 1465, 1258, 1106 cm$^{-1}$
Molecular Weight: 868
ESI-MS (30V): m/z (%) 869 [M+H]$^+$, 508 (100)
$^1$H NMR (CD$_3$OD, 400 MHz):δ 8.03 (s, 1H), 7.61 (d, J=6.7 Hz, 2H), 7.31 (d, J=6.7 Hz, 2H), 6.95-6.70 (m, 9H), 6.60 and 6.58 (s, 1H), 4.34-4.30 (m, 1H), 4.03-3.93 (m, 3H), 3.79-3.65 (m, 12H), 3.41-2.65 (m, 12H), 1.39 (s, 6H).

TEST EXAMPLE 1

Evaluation of Antioxidizing Activity in Free Radical Scavenging of 1,1-diphenyl-2-picryl-hydrazyl (DPPH)

An ethanolic solution of the stable nitrogen centered free radical 1,1-Diphenyl-2-picrylhydrazyl (DPPH, 100 µM) was incubated with the test compounds ($10^{-8}$-$10^{-4}$M or 1-100 µM) in 96-well plates, and then mixed thoroughly in a light-proof environment at room temperature. After 30 min, the absorbance (O.D.) was monitored spectrophotometrically at 517 nm. The activity in inhibiting free radical DPPH results in the decrease of absorbance.

FIG. 1 shows that the test compounds 1-2 exhibit activity in free radical scavenging of DPPH at a concentration higher than about $10^{-5}$ M. Accordingly, it can be confirmed that the compounds 1-2 and the salts thereof exhibit the activity in inhibiting free radical DPPH.

Figure 2:
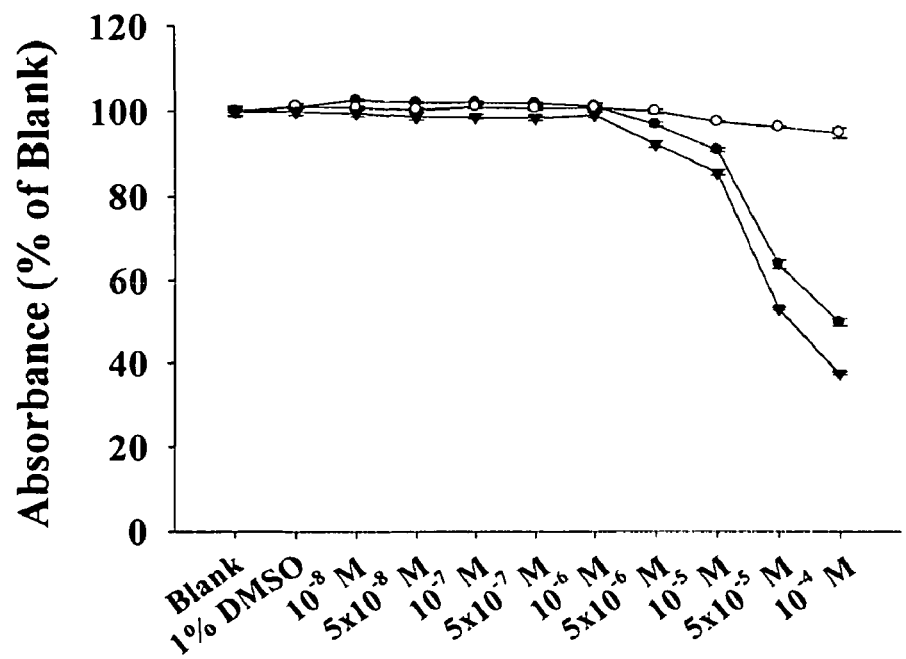
FIG. 2 shows a diagram of absorbance of DPPH versus the concentration of thaliporphine, atorvastatin and atorvastatin salt of thaliporphine (-●- for thaliporphine, -○- for atorvastatin, -▼- for atorvastatin salt of thaliporphine).

FIG. 2 shows that the atorvastatin salt of thaliporphine exhibits much higher activity in free radical scavenging of DPPH, in comparison with atorvastatin alone and thaliporphine alone.

Figure 3:
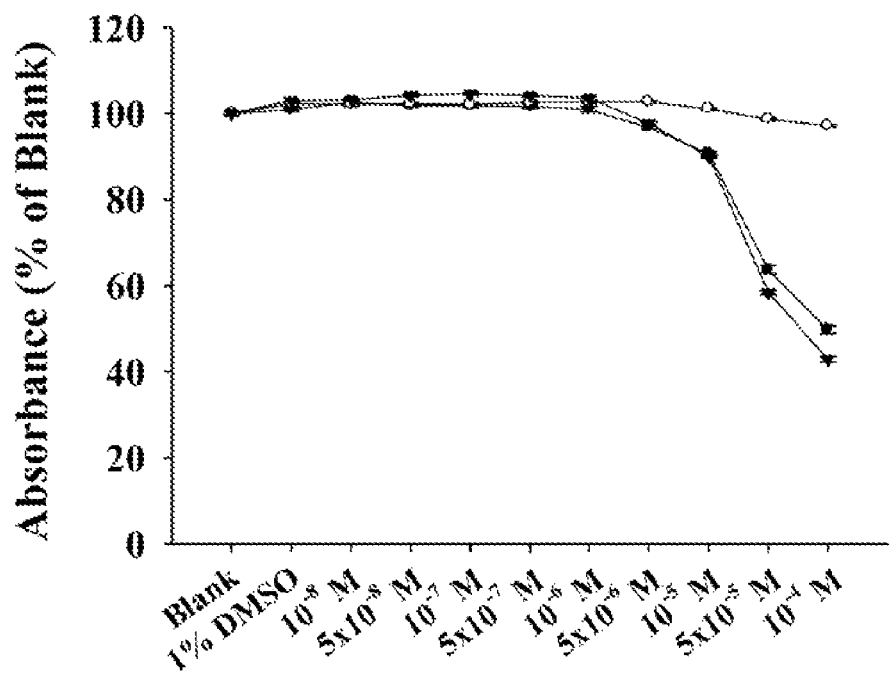
FIG. 3 shows a diagram of absorbance of DPPH versus the concentration of thaliporphine, telmisartan and telmisartan salt of thaliporphine (-●- for thaliporphine, -○- for telmisartan, -▼- for telmisartan salt of thaliporphine).

FIG. 3 shows that the telmisartan salt of thaliporphine exhibits much higher activity in free radical scavenging of DPPH, in comparison with telmisartan alone and thaliporphine alone.

Figure 4:
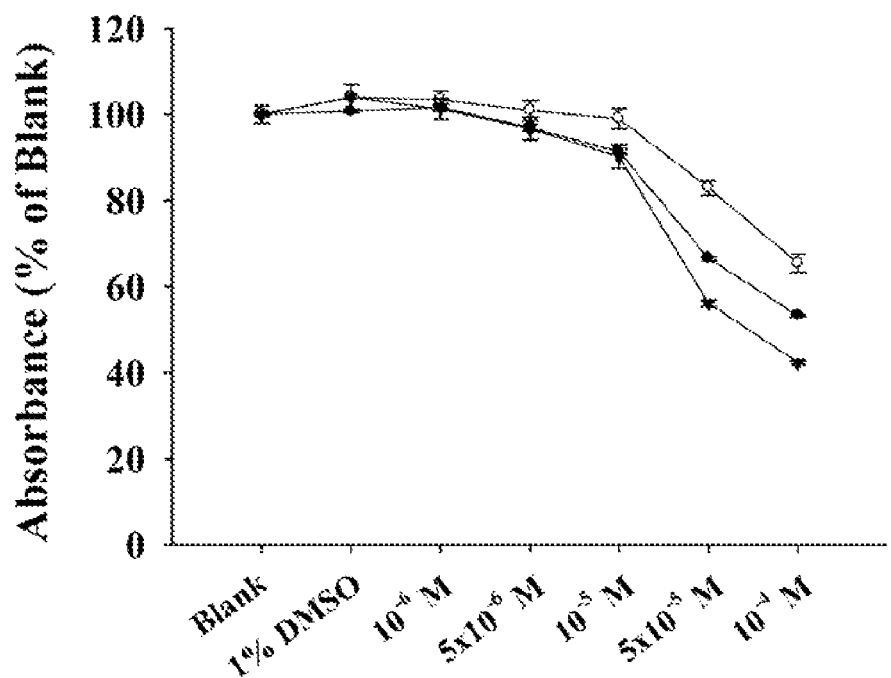
FIG. 4 shows a diagram of absorbance of DPPH versus the concentration of thaliporphine, captopril and captopril salt of thaliporphine (-●- for thaliporphine, -○- for captopril, -▼- for captopril salt of thaliporphine).

FIG. 4 shows that the captopril salt of thaliporphine exhibits much higher activity in free radical scavenging of DPPH, in comparison with captopril alone and thaliporphine alone.

Figure 5:
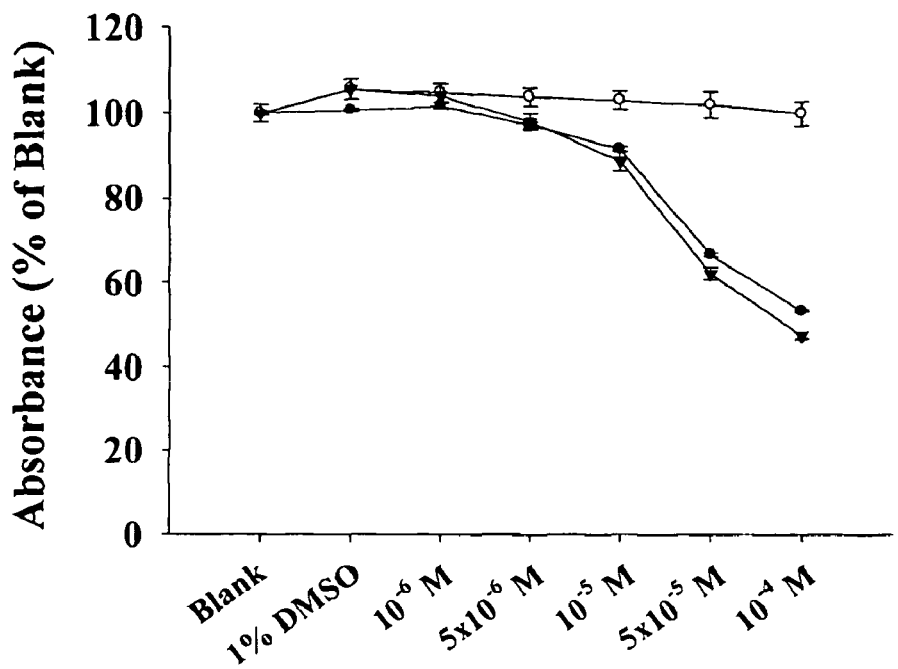
FIG. 5 shows a diagram of absorbance of DPPH versus the concentration of thaliporphine, bezafibrate and bezafibrate salt of thaliporphine (-●- for thaliporphine, -○- for bezafibrate, -▼- for bezafibrate salt of thaliporphine).

FIG. 5 shows that the bezafibrate salt of thaliporphine exhibits much higher activity in free radical scavenging of DPPH, in comparison with bezafibrate alone and thaliporphine alone.

Figure 6:
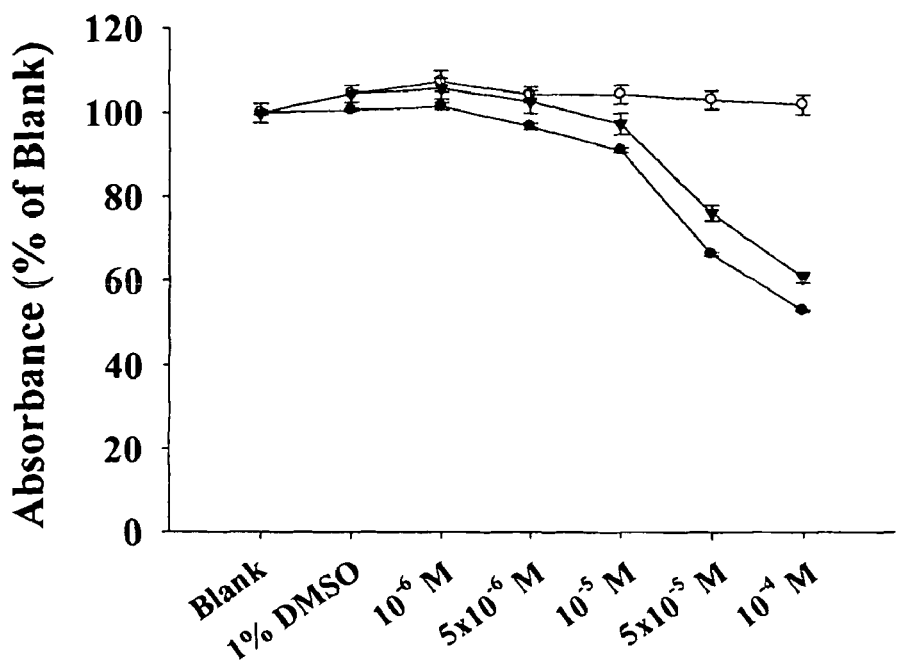
FIG. 6 shows a diagram of absorbance of DPPH versus the concentration of thaliporphine, nateglinide and nateglinide salt of thaliporphine (-●- for thaliporphine, -○- for nateglinide, -▼- for nateglinide salt of thaliporphine).

FIG. 6 shows that the nateglinide salt of thaliporphine exhibits much higher activity in free radical scavenging of DPPH, in comparison with nateglinide alone.

Figure 7:
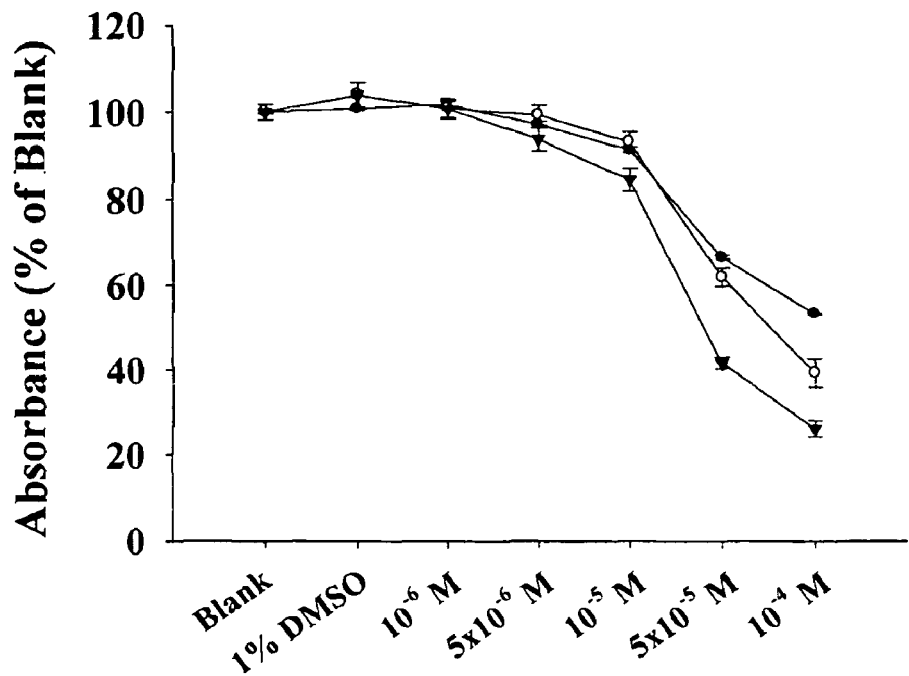
FIG. 7 shows a diagram of absorbance of DPPH versus the concentration of thaliporphine, acetylcysteine and acetylcysteine salt of thaliporphine (-●- for thaliporphine, -○- for acetylcysteine, -▼- for acetylcysteine salt of thaliporphine).

FIG. 7 shows that the acetylcysteine salt of thaliporphine exhibits much higher activity in free radical scavenging of DPPH, in comparison with acetylcysteine alone and thaliporphine alone.

Figure 8:
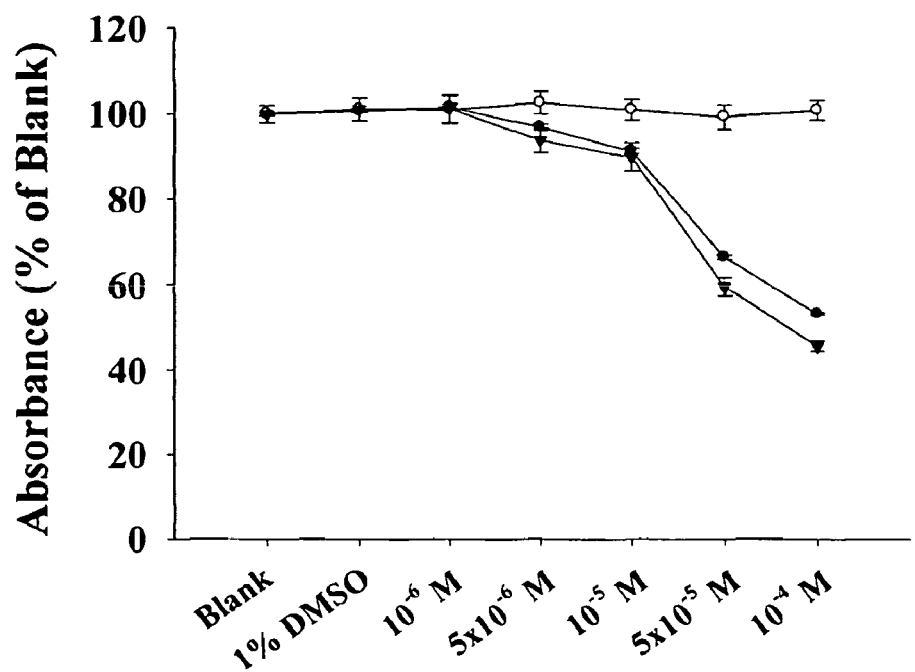
FIG. 8 shows a diagram of absorbance of DPPH versus the concentration of thaliporphine, salsalate and salsalate salt of thaliporphine (-●- for thaliporphine, -○- for salsalate, -▼- for salsalate salt of thaliporphine).

FIG. 8 shows that the salsalate salt of thaliporphine exhibits much higher activity in free radical scavenging of DPPH, in comparison with salsalate alone and thaliporphine alone.

Thereby, it can be confirmed that these novel salts of aporphine derivatives exhibit much higher activity in comparison with carboxyl group-containing agent alone and aporphine derivative alone.

TEST EXAMPLE 2

Evaluation of Protecting Activity from Peroxy Radical-Induced Damage

[Method A]

In order to evaluate the effect of test compounds in scavenging hydrophilic peroxy radical, the experiment was executed with reference to the method described by Tsuchiya et al. (Methods Enzymol 1992, 213: 460-472). In the experiment, peroxides will react with fluorescent substances and thus inflect observed fluorescence intensity. Thereby, the effect of test compounds in free radical scavenging can be evaluated by measuring the variation of the fluorescence intensity after the addition of test compounds.

First, to a silicate tube was added a phosphate solution (2 ml, pH 7.4), followed by the addition of β-phycoerythrin (5 nM) to increase relative fluorescence intensity. After 5 minutes, 2,2'-azobis (2-amidinopropane)dihydrochloride (25 mM, AAPH) was added therein. Subsequently, through a fluorescent spectrometry (Shimadzu RF-5301PC, Japan), the fluorescence intensity of β-phycoerythrin was measured by excitation at 540 nm and emission at 570 nm. Then, the test compounds ($5\times10^{-6}$ M) was further added therein to observe the variation of the fluorescence intensity, in which 0.1% DMSO was taken as a control group.

Figure 9:
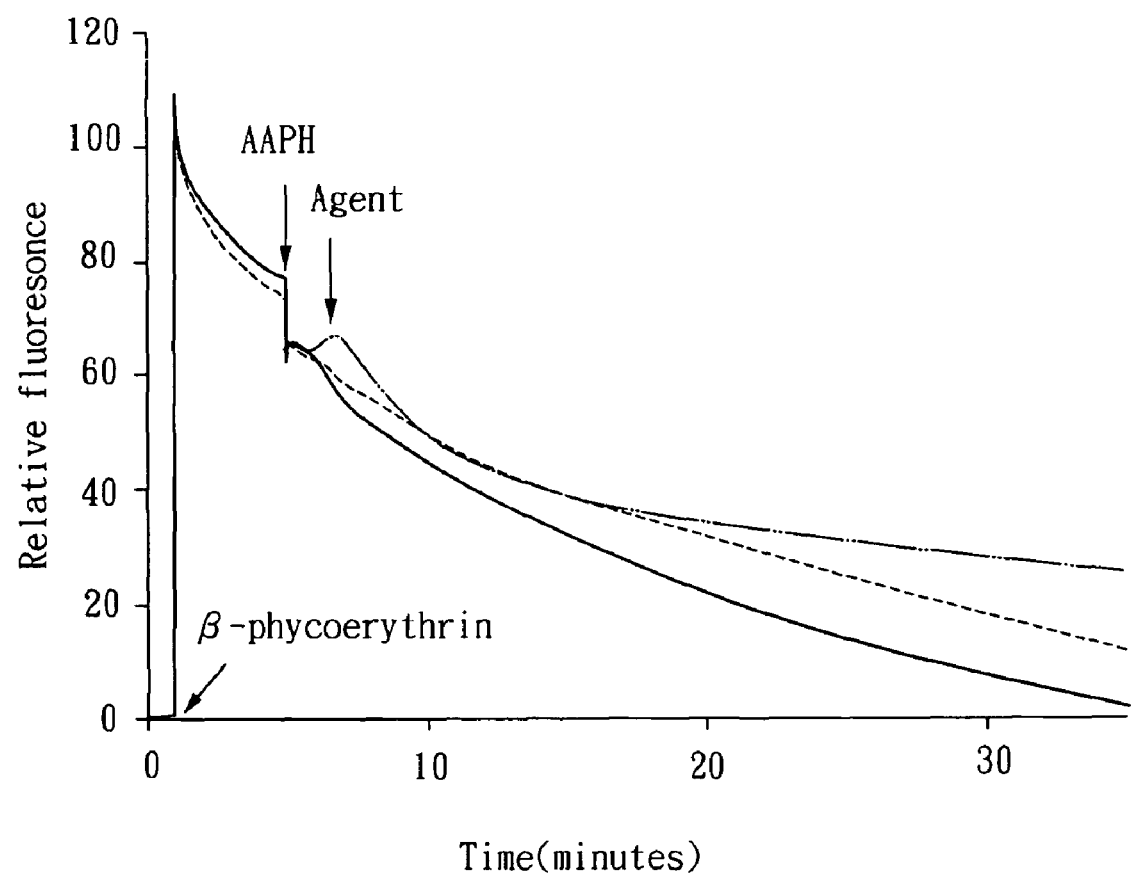
FIG. 9 shows a fluorescence decay dynamics of β-phycoerythin (——for 0.1% DMSO as a control group, - -- - for Compound 1 of $5 \times 10^{-6}$ M, --- for Compound 2 of $5 \times 10^{-6}$ M).

FIG. 9 shows that the test compounds 1-2 can protect β-phycoerythin from peroxy radical AAPH—induced damage, and thus delay β-phycoerythin fluorescence degradation. Thereby, it can be confirmed that the test compounds 1-2 and the salts thereof exhibit activity in free radical scavenging of APPH.

[Method B]

In order to evaluate the oxygen radical absorbing capacity of test compounds. The automated assay was carried out as described in a previous report by Gillespie and co-workers (Gillespie et al., 2007). The experiment was conducted at 37° C. under pH 7.4 condition with a blank sample in parallel. Briefly, 2, 2'-azobis (2-amidinopropane) dihydrochloride (AAPH) was used as a peroxyl generator. The final reaction mixture for each black microplat in a 96-well microplate assay contained 0.06 μM fluorescenin, 18.75 mM AAPH and appropriate test substance (1 μM) in 75 mM phosphate buffer. Test substance was directly dissolved in DMSO and diluted with 75 mM potassium phosphate buffer (pH 7.4) for analysis. The analyzer was programmed to record the fluorescence of fluorescenin every minute after the addition of AAPH. All fluorescent measurements are expressed relative to the initial reading (excitation at 485 nm and emission at 530 nm) on a FLUOstar Galaxy plate reader (Roche Diagnostic System Inc., Branchburg, N.J.). Raw data were exported from the Fluostar Galaxy software to an Excel (Microsoft, Roselle, Ill.) sheet for further calculations. All the reaction mixtures were prepared in duplicate, and at least three independent assays were performed for each sample. (Gillespie, K M et al., *Nature Protocols* 2007; 2: 867-870.)

Figure 10:
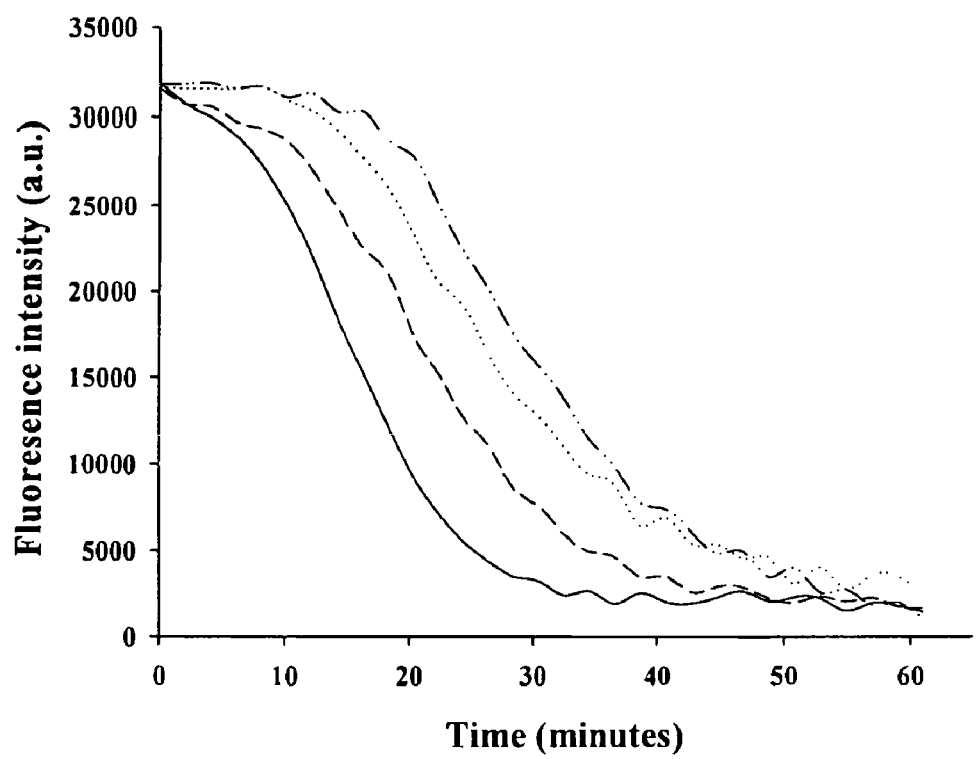
FIG. 10 shows a fluorescence decay dynamics of fluorescenin (——for 0.1% DMSO as a control group, ... for thaliporphine of $10^{-6}$ M, --- for atorvastatin of $10^{-6}$ M, - -- - for atorvastatin salt of thaliporphine of $10^{-6}$ M).

FIG. 10 shows that the atorvastatin salt of thaliporphine exhibits much higher activity in free radical scavenging of APPH, in comparison with atorvastatin alone and thaliporphine alone.

Figure 11:
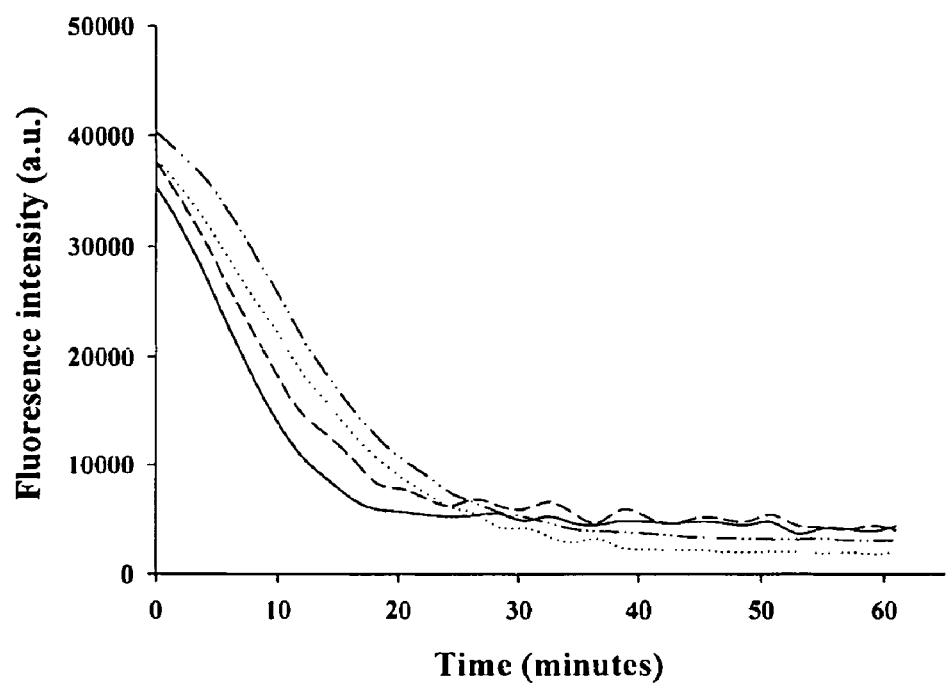
FIG. 11 shows a fluorescence decay dynamics of fluorescenin (——for 0.1% DMSO as a control group, ... for thaliporphine of $10^{-6}$ M, --- for captopril of $10^{-6}$ M, - -- - for captopril salt of thaliporphine of $10^{-6}$ M).

FIG. 11 shows that the captopril salt of thaliporphine exhibits much higher activity in free radical scavenging of APPH, in comparison with captopril alone and thaliporphine alone.

Figure 12:
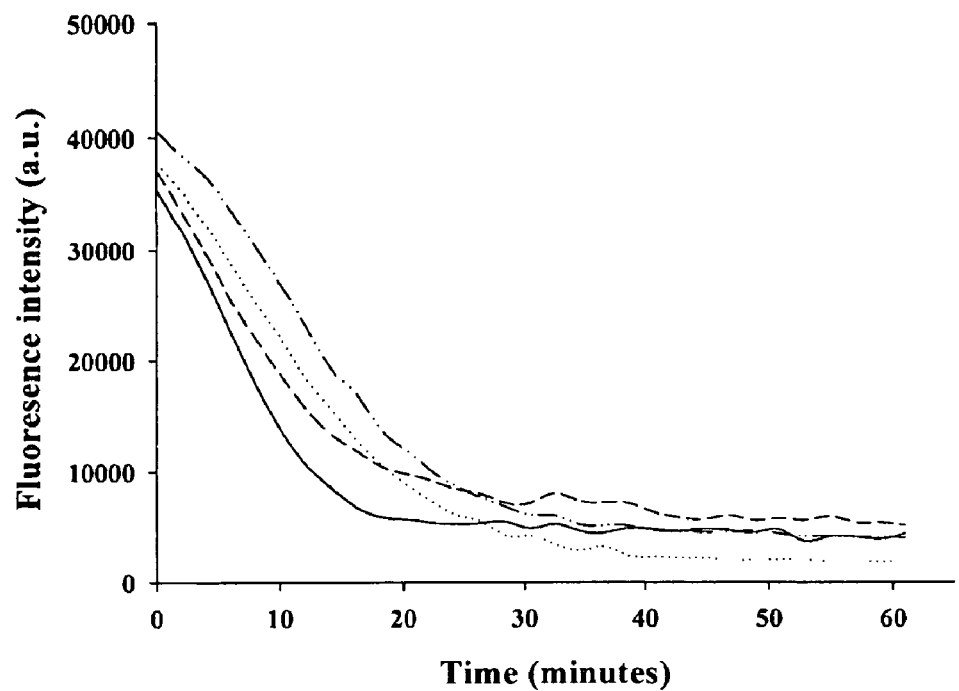
FIG. 12 shows a fluorescence decay dynamics of fluorescenin (——for 0.1% DMSO as a control group, ... for thaliporphine of $10^{-6}$ M, --- for bezafibrate of $10^{-6}$ M, - -- - for bezafibrate salt of thaliporphine of $10^{-6}$ M).

FIG. 12 shows that the bezafibrate salt of thaliporphine exhibits much higher activity in free radical scavenging of APPH, in comparison with bezafibrate alone and thaliporphine alone.

Figure 13:
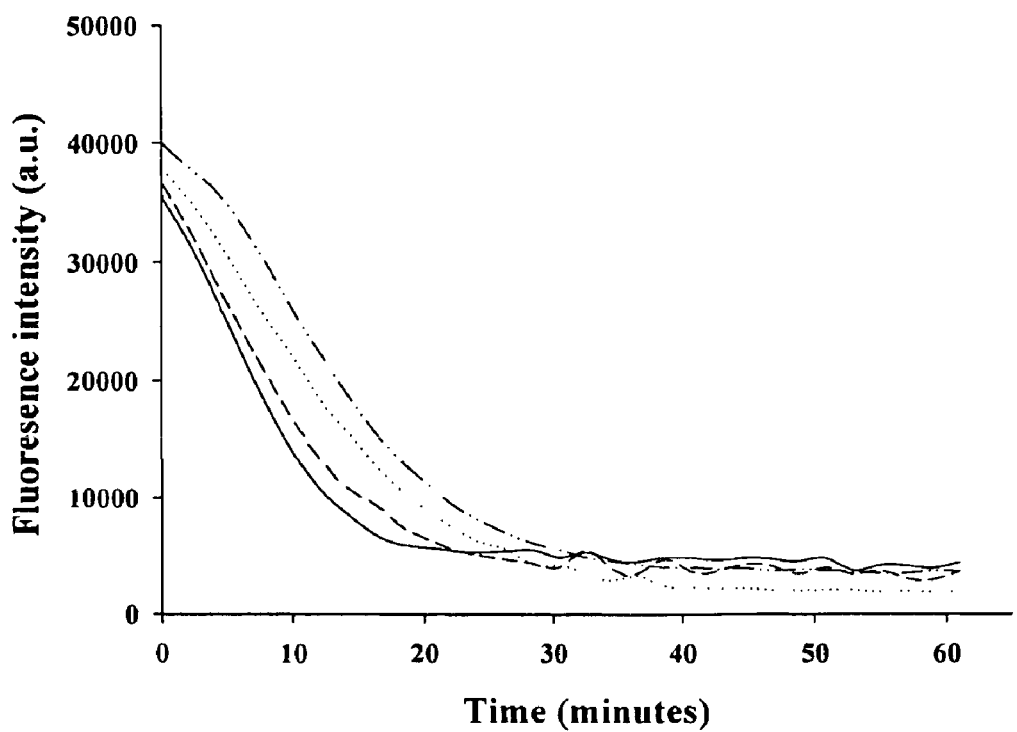
FIG. 13 shows a fluorescence decay dynamics of fluorescenin (——for 0.1% DMSO as a control group, ... for thaliporphine of $10^{-6}$ M, --- for nateglinide of $10^{-6}$ M, - -- - for nateglinide salt of thaliporphine of $10^{-6}$ M).

FIG. 13 shows that the nateglinide salt of thaliporphine exhibits much higher activity in free radical scavenging of APPH, in comparison with nateglinide alone and thaliporphine alone.

Figure 14:
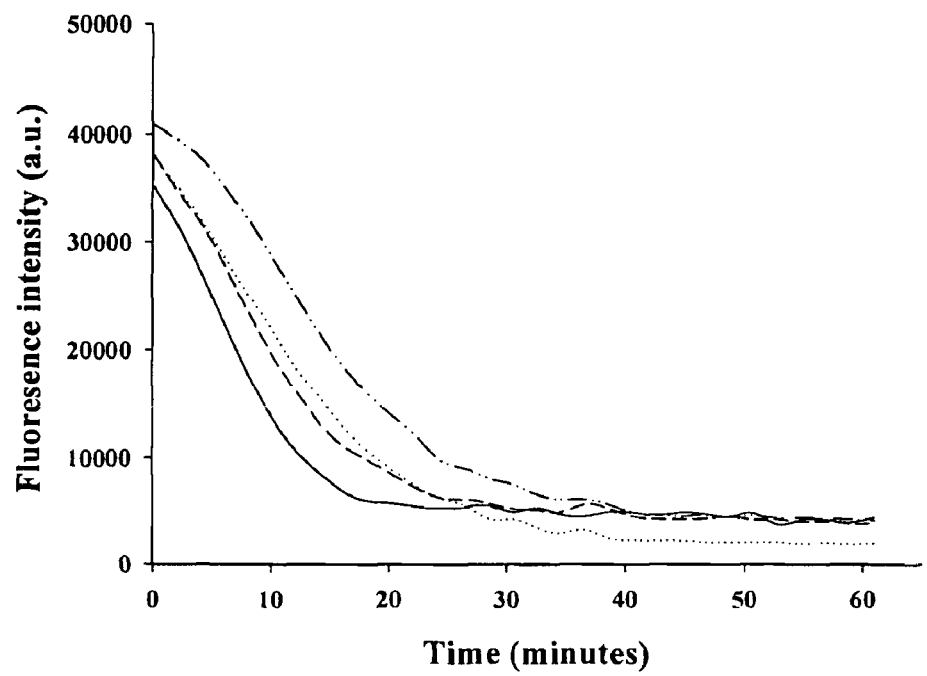
FIG. 14 shows a fluorescence decay dynamics of fluorescenin (——for 0.1% DMSO as a control group, ... for thaliporphine of $10^{-6}$ M, --- for acetylcysteine of $10^{-6}$ M, - -- - for acetylcysteine salt of thaliporphine of $10^{-6}$ M).

FIG. 14 shows that the acetylcysteine salt of thaliporphine exhibits much higher activity in free radical scavenging of APPH, in comparison with acetylcysteine alone and thaliporphine alone.

Figure 15:
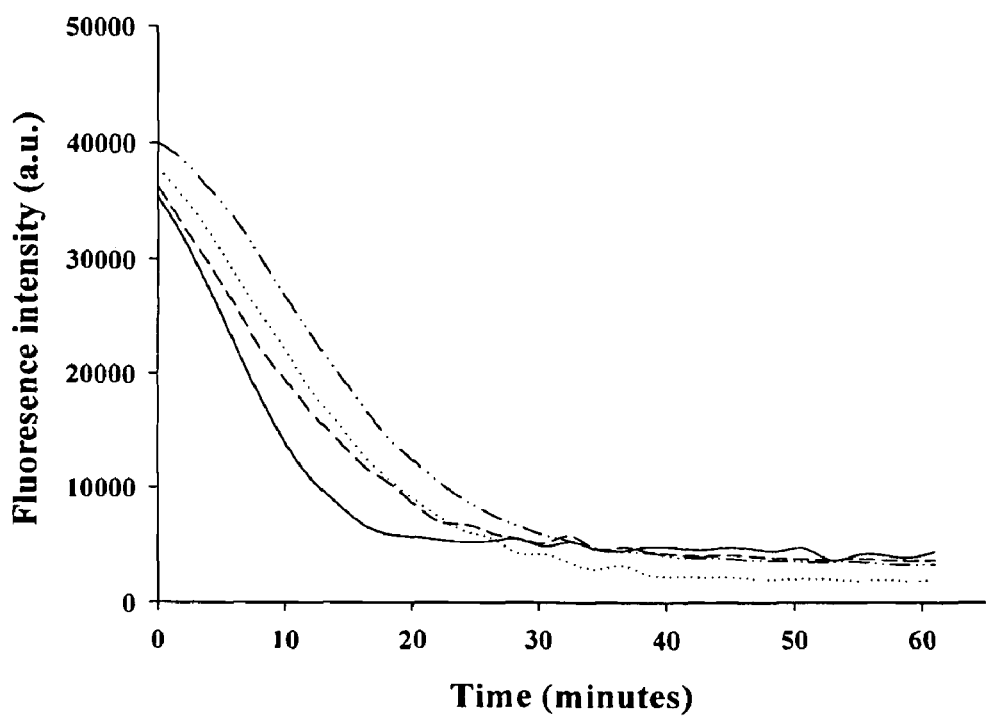
FIG. 15 shows a fluorescence decay dynamics of fluorescenin (——for 0.1% DMSO as a control group, ... for thaliporphine of $10^{-6}$ M, --- for salsalate of $10^{-6}$ M, - -- - for salsalate salt of thaliporphine of $10^{-6}$ M).

FIG. 15 shows that the salsalate salt of thaliporphine exhibits much higher activity in free radical scavenging of APPH, in comparison with salsalate alone and thaliporphine alone.

Figure 16:
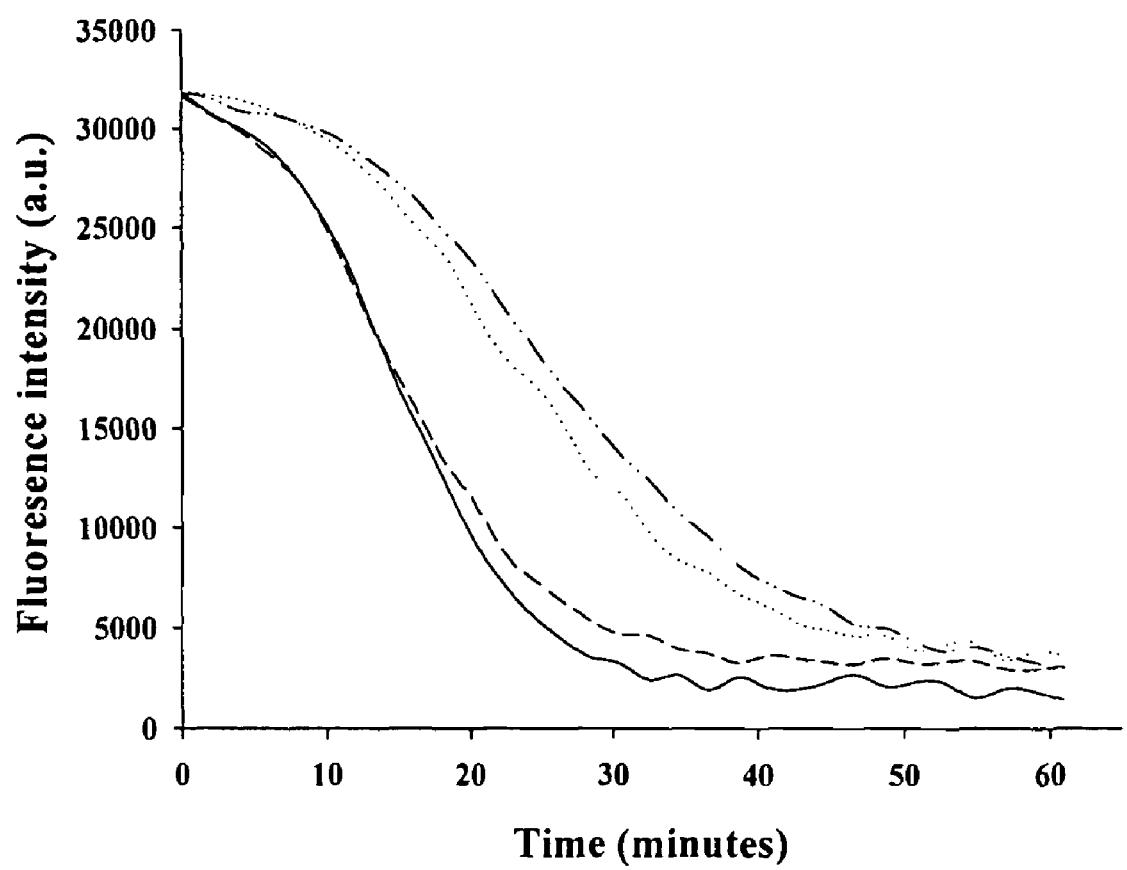
FIG. 16 shows a fluorescence decay dynamics of fluorescenin (——for 0.1% DMSO as a control group, ... for glaucine of $10^{-6}$ M, --- for ozagrel of $10^{-6}$ M, - -- - for ozagrel salt of glaucine of $10^{-6}$ M).

FIG. 16 shows that the ozagrel salt of glaucine exhibits much higher activity in free radical scavenging of APPH, in comparison with ozagrel alone and glaucine alone.

Thereby, it can be confirmed that these novel salts of aporphine derivatives exhibit much higher activity in comparison with carboxyl group-containing agent alone and aporphine derivative alone.

Thereby, it can be confirmed that these novel salts of aporphine derivatives exhibit more efficient activity in comparison with carboxyl group-containing agent alone and aporphine derivative alone.

TEST EXAMPLE 3

Evaluation of Activity in Inhibiting Lipid Peroxidase

The assay was executed with reference to the method described in *Biochem Biophys Res Commun*. Mar. 28, 1986; 135(3): 1015-21. The assay conditions are shown as follows, and the results are shown in Table 1.

Assay Conditions:
(a) Source: Dunkin Hartley Guinea pig liver microsomes
(b) Substrate: Polyunsaturated fatty acid
(c) Vehicle: 1% DMSO
(d) Pre-Incubation Time/Temp: 15 minutes/37° C.

(e) Incubation Time/Temp: 20 minutes/37° C.
(f) Incubation Buffer: 0.25 M Potassium Phosphate, pH 7.4, 0.1 mM EDTA
(g) Quantitation Method: Spectrophotometric quantitation of Malondialdehyde

TABLE 1

| Compound No. | Species | Concentration | Inhibition (%) |
|---|---|---|---|
| 1 | guinea pig | 10 μM | 64 |
| 2 | guinea pig | 10 μM | 70 |

In view of the experimental results shown in Table 1, it can be confirmed that the test compounds 1-2 and the salts thereof exhibit activity in inhibiting lipid peroxidase.

TEST EXAMPLE 4

Evaluation of Protecting Activity in Vascular Smooth Muscle Cells

Procedure

The vascular smooth muscle cells of rats ($2 \times 10^4$ cells/mL×1 mL) were quantitatively seeded in 24-well plates, and cultured in Dulbecco's modified Eagle medium (DMEM) with 10% fetal bovine serum (FBS) for 24 hours to achieve cell adhesion. After cell adhesion, the DMEM medium with 10% fetal bovine serum was replaced with a fresh DMEM medium with 0.1% fetal bovine serum to perform cell culture for 48 hours.

Next, each test compound was added in the cultures (final concentration: 0.1, 1, 10 μM). After 30 minutes, $H_2O_2$ (200 μM) was added therein to perform reaction for 24 hours in an incubator. Subsequently, in a light-proof environment, MTT (100 μL) was added into each well to perform reaction at 37° C. for 3 hours. The supernatant liquor was removed and then isopropanol (500 μL) was added, followed by shaking for 10 minutes. After standing for 10 minutes, supernatant liquor (200 μL) was transferred into 96-well plates. Finally, the absorbance value (O.D.) was monitored at 540 nm (OD540) and 630 nm (OD630). Based on the measured absorbance values (OD540-OD630), the effect of these test compounds on cell growth can be evaluated, as shown in FIG. 3.

Experimental Results

Rat vascular smooth muscle cells were incubated with various concentrations of $H_2O_2$ for 24 hours at 37° C. Concentration-dependent cytotoxicity of $H_2O_2$ was observed. $H_2O_2$ at a concentration larger than 100 μM resulted in cell death.

Figure 17:
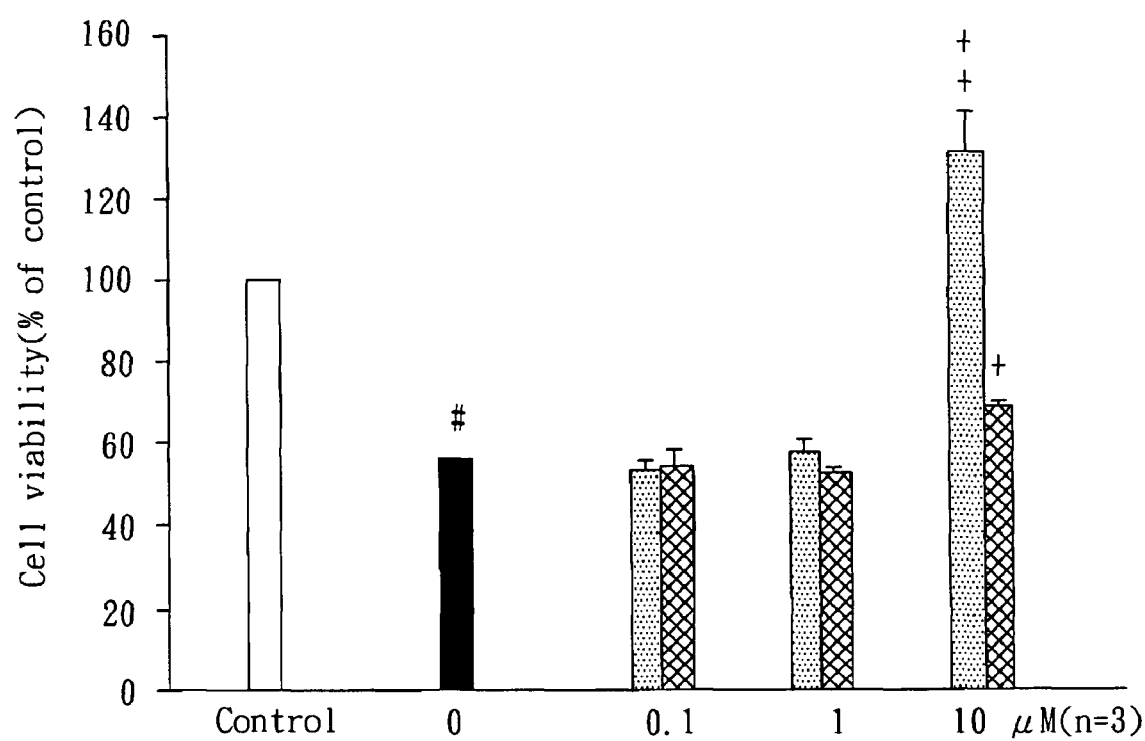
FIG. 17 shows a diagram of cell viability versus the concentration of Compounds 1 and 2 (□ for a control group, ■ for $H_2O_2$ of 200 μM, ▩ for Compound 1+$H_2O_2$ of 200 μM, ▨ for Compound 2+$H_2O_2$ of 200 μM).

Various concentrations of test compounds (Compounds 1 and 2) were incubated with rat vascular smooth muscle cells for 30 minutes. Then, $H_2O_2$ (200 μM) was added to the cells for 24 hours. It was found that $H_2O_2$ (200 μM) significantly decrease the cell number (#P<0.05). The test compound 2 (10 μM) slightly inhibited $H_2O_2$-induced damage to vascular smooth muscle cells. The test compound 1 (10 μM) significantly inhibited $H_2O_2$-induced damage to vascular smooth muscle cells and thereby increased cells survival rate (**P <0.01), as shown in FIG. 17.

In view of the results of Test Examples 1-4, it can be confirmed that the pharmaceutically acceptable salts provided by the present invention are effective in inhibiting lipid peroxidase, exerting the free radical scavenging activities and protecting blood vessel smooth muscle cells and thus can reduce the oxidative stress.

Although the present invention has been explained in relation to its preferred embodiment, it is to be understood that many other possible modifications and variations can be made without departing from the scope of the invention as hereinafter claimed.

What is claimed is:

1. A pharmaceutically acceptable compound, which is a 1:1 salt of a basic compound of the following formula (I) and a carboxyl group-containing acidic agent

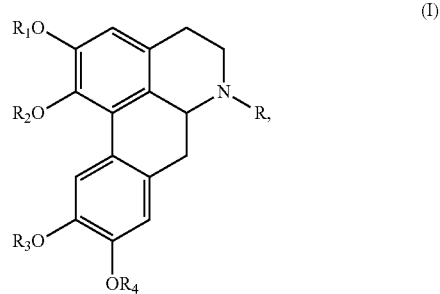

(I)

wherein,
each of $R_1$, $R_2$, $R_3$ and $R_4$, independently, is hydrogen, or $C_{1-6}$ alkyl;
R is hydrogen, $C_{1-6}$ alkyl, —C(O)$R_5$ or $C_{1-6}$ alkyl substituted by the following group: —C(O)OR$_6$, —C(O)NR$_6$R$_7$, —OR$_6$, —NR$_6$R$_7$, $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl;
$R_5$ is $C_{4-9}$ heteroaryl containing at least one heteroatom selected from the group consisting of N, O and S, or $C_{1-6}$ alkyl substituted by —NR$_6$R$_7$ or $C_{4-9}$ heterocyclyl containing at least one heteroatom selected from the group consisting of N, O and S;
each of $R_6$ and $R_7$, independently, is hydrogen, $C_{1-6}$ alkyl, $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl;
and the carboxyl group-containing acidic agent is selected from the group consisting of atorvastatin, telmisartan, captopril, bezafibrate, repaglinide, acetylcytsteine, chromocarb, nateglinide, salsalate, and ozagrel.

2. The pharmaceutically acceptable compound of claim 1, wherein the carboxyl group-containing acidic agent is selected from the group consisting of atorvastatin, telmisartan, captopril, bezafibrate, repaglinide, acetylcysteine, chromocarb, nateglinide, and salsalate.

3. The pharmaceutically acceptable compound of claim 1, wherein R is hydrogen, $C_{1-6}$ alkyl, —C(O)$R_5$, or $C_{1-6}$ alkyl substituted by —C(O)OR$_6$, —C(O)NR$_6$R$_7$, —OR$_6$ or $C_{4-9}$ heteroaryl containing at least one heteroatom selected from the group consisting of N, O and S.

4. The pharmaceutically acceptable compound of claim 3, wherein R is hydrogen, $C_{1-6}$ alkyl, —C(O)$R_5$, or $C_{1-6}$ alkyl substituted by —C(O)OR$_6$, —C(O)NR$_6$R$_7$, $C_{4-9}$ heteroaryl containing at least one heteroatom selected from the group consisting of N, O and S, one —OR$_6$, or both of hydroxyl and —O—C$_{6-10}$ aryl unsubstituted or substituted by at least one selected from the group consisting of halogen, hydroxyl, C$_{1-6}$ alkoxy and C$_{1-6}$ alkyl.

5. The pharmaceutically acceptable compound of claim 4, wherein R is hydrogen, C$_{1-6}$ alkyl, —C(O)R$_5$, or C$_{1-6}$ alkyl substituted by C(O)NR$_6$R$_7$, C$_{4-9}$ heteroaryl containing at least one heteroatom selected from the group consisting of N, O and S, one —OR$_6$, or both of hydroxyl and —O—C$_{6-10}$ aryl unsubstituted or substituted by at least one selected from the group consisting of halogen, hydroxyl, C$_{1-6}$ alkoxy and C$_{1-6}$ alkyl.

6. The pharmaceutically acceptable compound of claim 5, wherein R$_6$ is C$_{4-9}$ heteroaryl containing at least one heteroatom selected from the group consisting of N, O and S, C$_{4-9}$ heterocyclyl containing at least one heteroatom selected from the group consisting of N, O and S, or C$_{6-10}$ aryl unsubstituted or substituted by at least one selected from the group consisting of halogen, hydroxyl, C$_{1-6}$ alkoxy and C$_{1-6}$ alkyl, and R$_7$ is hydrogen.

7. The pharmaceutically acceptable compound of claim 6, wherein R is hydrogen, C$_{1-6}$ alkyl,

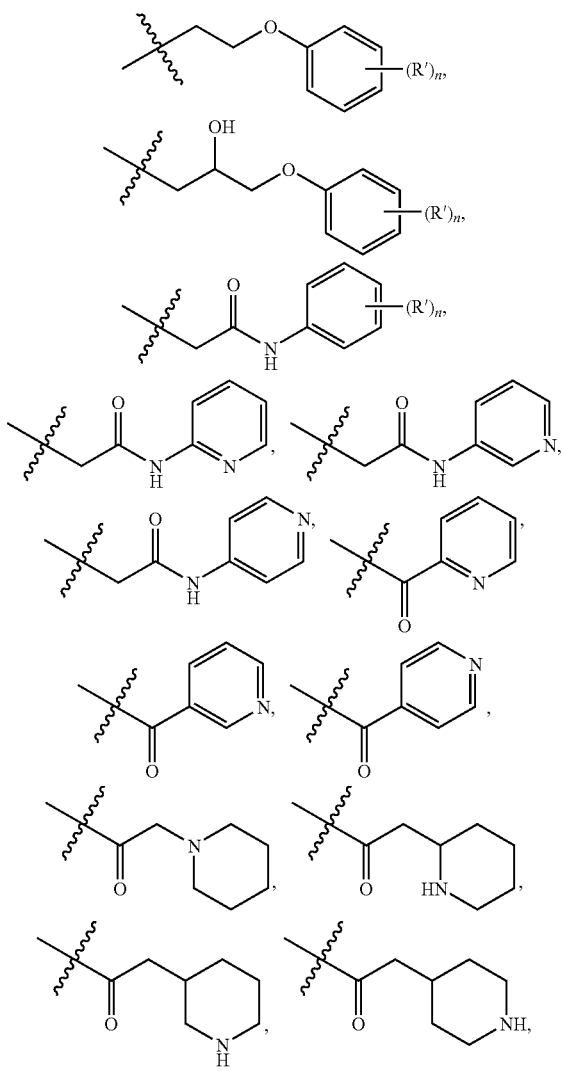

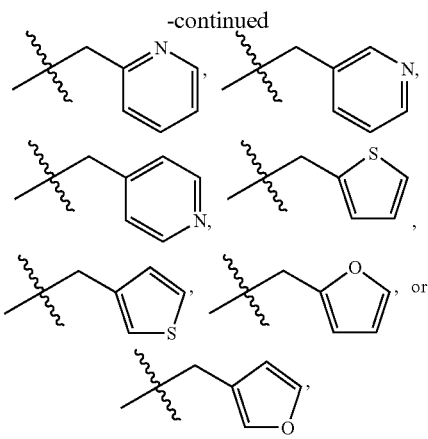

n being an integer from 0 to 5, and R' independently being halogen, hydroxyl, C$_{1-6}$ alkoxy or C$_{1-6}$ alkyl.

8. A method for preparing the pharmaceutically acceptable compound of claim 1, comprising:
mixing the compound of the formula (I) and the carboxyl group-containing acidic agent to form a mixture; and
pulverizing the mixture by a physical-mechanical means to form the pharmaceutically acceptable compound.

9. The method of claim 8, wherein the carboxyl group-containing acidic agent is selected from the group consisting of atorvastatin, telmisartan, captopril, bezafibrate, repaglinide, acetylcysteine, chromocarb, nateglinide, salsalate, and ozagrel.

10. The method of claim 8, wherein R is hydrogen, C$_{1-6}$ alkyl, or C$_{1-6}$ alkyl substituted by —C(O)NR$_6$R$_7$, C$_{4-9}$ heteroaryl containing at least one heteroatom selected from the group consisting of N, O and S, one —OR$_6$, or both of hydroxyl and —O—C$_{6-10}$ aryl unsubstituted or substituted by at least one selected from the group consisting of halogen, hydroxyl, C$_{1-6}$ alkoxy and C$_{1-6}$ alkyl.

11. The method of claim 10, wherein R is hydrogen, C$_{1-6}$ alkyl,

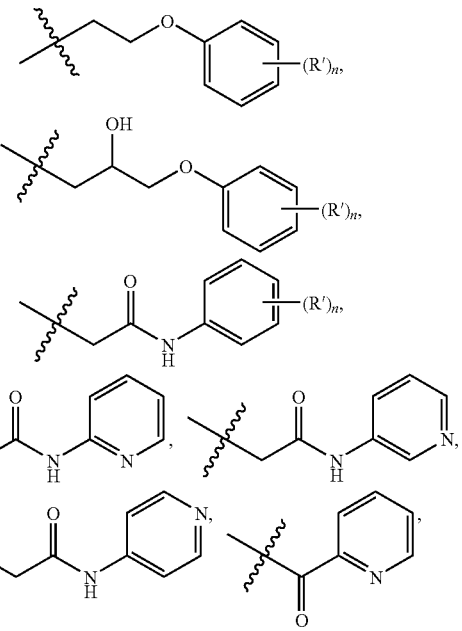

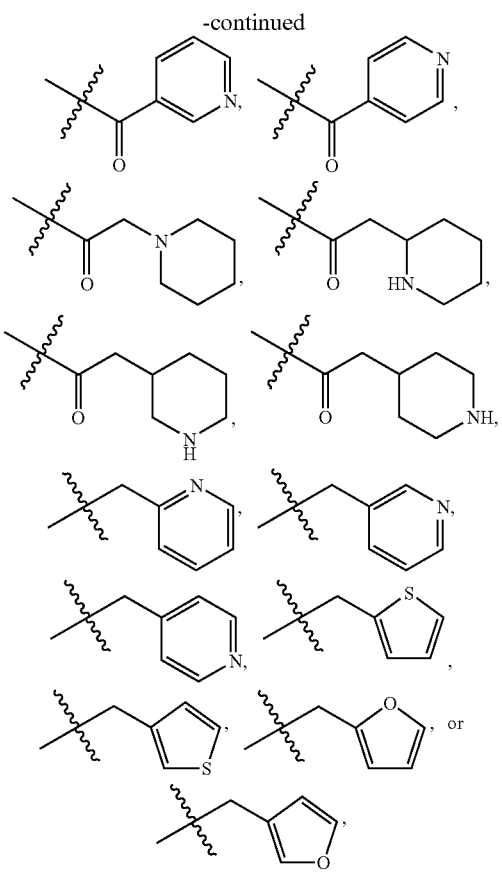

n being an integer from 0 to 5, and R' independently being halogen, hydroxyl, $C_{1-6}$ alkoxy or $C_{1-6}$ alkyl.

12. A method for preparing the pharmaceutically acceptable compound of claim 1, comprising:
  dissolving the compound of the formula (I) and the carboxyl group-containing acidic agent in a first solvent to form a solution; and
  removing the first solvent from the solution or mixing the solution with a second solvent to obtain the pharmaceutically acceptable compound.

13. The method of claim 12, wherein the carboxyl group-containing acidic agent is selected from the group consisting of atorvastatin, telmisartan, captopril, bezafibrate, repaglinide, acetylcysteine, chromocarb, nateglinide, and salsalate.

14. The method of claim 12, wherein R is hydrogen, $C_{1-6}$ alkyl, —C(O)$R_5$, or $C_{1-6}$ alkyl substituted by —C(O)NR$_6$R$_7$, $C_{4-9}$ heteroaryl containing at least one heteroatom selected from the group consisting of N, O and S, one —OR$_6$, or both of hydroxyl and —O—C$_{6-10}$ aryl unsubstituted or substituted by at least one selected from the group consisting of halogen, hydroxyl, $C_{1-6}$ alkoxy and $C_{1-6}$ alkyl.

15. The method of claim 14, wherein R is hydrogen, $C_{1-6}$ alkyl, n being an integer from 0 to 5, and R' independently being halogen, hydroxyl, $C_{1-6}$ alkoxy or $C_{1-6}$ alkyl.

16. The pharmaceutically acceptable compound of claim 1, wherein $R_4$ is $C_{1-6}$ alkyl.

17. The pharmaceutically acceptable compound of claim 16, wherein $R_4$ is methyl.

18. The pharmaceutically acceptable compound of claim 1, wherein each of $R_1$, $R_2$, $R_3$ and $R_4$ is methyl.

19. The pharmaceutically acceptable compound of claim 1, wherein each of $R_1$, $R_3$ and $R_4$ is methyl, and $R_2$ is hydrogen.

* * * * *